United States Patent
Compton et al.

(10) Patent No.: US 8,586,034 B2
(45) Date of Patent: Nov. 19, 2013

(54) CYTOMEGALOVIRUS DISINTEGRIN-LIKE PEPTIDES

(75) Inventors: Teresa Compton, Madison, WI (US); Adam Lloyd Feire, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 873 days.

(21) Appl. No.: 12/369,650

(22) Filed: Feb. 11, 2009

(65) Prior Publication Data
US 2011/0117109 A1 May 19, 2011

Related U.S. Application Data

(62) Division of application No. 11/127,601, filed on May 12, 2005, now Pat. No. 7,491,490.

(60) Provisional application No. 60/570,260, filed on May 12, 2004.

(51) Int. Cl.
*A61K 39/395* (2006.01)
*A61K 39/00* (2006.01)
*A61K 39/42* (2006.01)
*A61K 39/12* (2006.01)
*A61K 39/35* (2006.01)

(52) U.S. Cl.
USPC ............... 424/130.1; 424/204.1; 424/229.1; 424/230.1; 424/139.1; 424/141.1; 424/147.1; 424/159.1

(58) Field of Classification Search
None
See application file for complete search history.

(56) References Cited

FOREIGN PATENT DOCUMENTS

WO    WO 87/05326    *    9/1987

OTHER PUBLICATIONS

Lucas, et al. Rapid diagnosis of cytomegalovirus by indirect immunofluorescence assay with monoclonal antibody F6b in a commercially available kit. J. Clin. Microbiol. 1989, 27(2):367.*
Meyer-Koenig, et al. (GenBank: AJ236815.1 submitted Feb. 16, 1999).*
Throsby, et al. Heterosubtypic Neutralizing Monoclonal Antibodies Cross-Protective against H5N1 and H1N1 Recovered from Human IgM+ Memory B CellsPLoS One. 2008; 1-15.*
Akula, S.M., Pramod, N.P., Wang, F.Z. & Chandran, B. Integrmn alpha3betal (CD 49c/29) is a cellular receptor for Kaposis sarcoma-associated herpesvirus (KSHV/HHV8) entry into the target cells. *Cell* 108, 407-19 (2002).
Almeida, E.A. et al. Mouse egg integrin alpha 6 beta 1 functions as a sperm receptor. *Cell* 81, 1095-104 (1995).
Bergelson, J.M., Shepley, M.P., Chan, B.M., Hemler, M.E. & Finberg, R.W. Identification of the integrin VLA-2 as a receptor for echovirus 1. *Science* 255, 1718-20 (1992).
Bergelson, J.M. et al. Infection by echoviruses 1 and 8 depends on the alpha 2 subunit of human VLA-2. *J Virol* 67, 6847-52 (1993).

(Continued)

*Primary Examiner* — Zachariah Lucas
*Assistant Examiner* — Stuart W Snyder
(74) *Attorney, Agent, or Firm* — Joseph T. Leone, Esq.; DeWitt Ross & Stevens S.C.

(57) ABSTRACT

The present invention relates to methods and compositions for inhibiting the entry of viruses, such as herpesviruses into a host cell. A conserved viral integrin-binding gB disintegrin-like domain has been identified that engages integrins and facilitates viral internalization into the host cell. Therefore, methods and compositions, such as antiviral agents encompassing the conserved gB disintegrin-like domain and antibodies thereto are described. These active agents interfere with the interaction between virions and cellular integrins, thereby inhibiting viral infection of a host cell.

25 Claims, 17 Drawing Sheets

(56) References Cited

OTHER PUBLICATIONS

Berman, A.E. & Kozlova, N.J. Integrins: structure and functions. *Membr Cell Biol* 13, 207-44 (2000).

Boissy, P., Machuca, I., Pfaff, M., Ficheux, D. & Jurdic, P. Aggregation of mononucleated precursors triggers cell surface expression of alphavbeta3 integrin, essential to formation of osteoclast-like multinucleated cells. *J Cell Sci* 111 (Pt 17),2563-74 (1998).

Boyle, K.A., Pietropaolo, R.L. & Compton, T. Engagement of the cellular receptor for glycoprotein B of human cytomegalovirus activates the interferon responsive pathway. *Mol Cell Biol* 19, 3607-13 (1999).

Cary, L.A., Han, D.C. & Guan, J.L. Integrin.mediated signal transduction pathways. *HistoiHistopathol* 14, 1001-9 (1999).

Chang, H.H. et al. Facilitation of cell adhesion by immobilized dengue viral nonstructural protein 1 (NS 1): arginine-glycine-aspartic acid structural mimicry within the dengue viral NS1 antigen. *J Infect Dis* 186, 743-5 1 (2002).

Ciarlet, M. et al. VLA-2 (alpha2beta1) integrin promotes rotavirus entry into cells but is not necessary for rotavirus attachment. *J Virol* 76, 1109-23 (2002).

Ciocco-Schmitt, G.M. et al. Identification and characterization of novel murine cytomegalovirus Ml 12-113 (el) gene products. *Virology* 294, 199-208 (2002).

Compton, T., Nepomuceno, R.R. & Nowlin, D.M. Human cytomegalovirus penetrates host cells by pH-independent fusion at the cell surface. *Virology* 191, 387-95 (1992).

Compton, T., Nowlin, D.M. & Cooper, N.R. Initiation of human cytomegalovirus infection requires initial interaction with cell surface heparan sulfate. *Virology* 193, 834-41 (1993).

Compton, T. et al. Human cytomegalovirus activates inflammatory cytokine responses via CD14 and Toll-like receptor 2. *J Virol* 77, 45 88-96 (2003).

Diosi, P., Babusceac, L. & David, C. Cytomegalovirus type cytopathic changes in spontaneously degenerating human embryonic cell cultures. *Nature* 214, 4 19-20 (1967).

Eto, K. et al. Functional classification of ADAMS based on a conserved motif for binding to integrin alpha 9beta 1: implications for sperm-egg binding and other cell interactions. *J Biol Chem* 277, 17804-10 (2002).

Feire, A.L. et al. (2004) Cellular integrins function as entry receptors for human cytomegalovirus via a highly conserved disintegrin-like domain. *Proc Natl Acad Sci USA* 101 (43), 15470-15475.

Gerna, G. et al. Human cytomegalovirus replicates abortively in polymorphonuclear leukocytes after transfer from infected endothelial cells via transient microfusion events. *J Virol* 74, 5629-3 8 (2000).

Gicklhorn, D., Eickmann, M., Meyer, G., Ohlin, M. & Radsak, K. Differential effects of glycoprotein B epitope-specific antibodies on human cytomegalovirus induced cell-cell fusion. *J Gen Virol* 84, 1859-62 (2003).

Graham, K.L. et al. Integrin-using rotaviruses bind alpha2beta1 integrin alpha2 I domain via VP4 DGE sequence and recognize alphaXbeta2 and alphaVbeta3 by using VP7 during cell entry. *J Virol* 77, 9969-78 (2003).

Henry, S.C. et al. Enhanced green fluorescent protein as a marker for localizing murine cytomegalovinis in acute and latent infection. *J Virol Methods* 89, 6 1-73 (2000).

Ibanez, C.E., Schrier, R., Ghazal, P., Wiley, C. & Nelson, J.A. Human cytomegalovirus productively infects primary differentiated macrophages. *J Virol* 65, 6581-8 (1991).

Jones, P.L., Crack, J. & Rabinovitch, M. Regulation of tenascin-C, a vascular smooth muscle cell survival factor that interacts with the alpha v beta 3 integrin to promote epidermal growth factor receptor phosphorylation and growth. *J Cell Biol* 139, 279-93 (1997).

Kowalik, T.F. et al. Multiple mechanisms are implicated in the regulation of NFkappa B activity during human cytomegalovirus infection. *Proc Natl Acad Sci USA* 90, 1107-11 (1993).

Lantto, J., Fletcher, J.M. & Ohlin, M. Binding characteristics determine the neutralizing potential of antibody fragments specific for antigenic domain 2 on glycoprotein B of human cytomegalovirus. *Virology* 305, 20 1-9 (2003).

Ljungman, P. Cytomegalovirus infections in transplant patients. *Scand Infect Dis Suppi* 100, 59-63 (1996).

McNally, A.K. & Anderson, J.M. Beta1 and beta2 integrins mediate adhesion during macrophage fusion and multinucleated foreign body giant cell formation. *Am J Pathol* 160, 621-30 (2002).

Miyamoto, S., Teramoto, H., Gutkind, J.S. & Yamada, K.M. Integrins can collaborate with growth factors for phosphorylation of receptor tyrosine kinases and MAP kinase activation: roles of integrin aggregation and occupancy of receptors. *J Cell Biol* 135, 1633-42 (1996).

Moro, L. et al. Integrins induce activation of EGF receptor: role in MAP kinase induction and adhesion-dependent cell survival. *Embo J* 17, 6622-32 (1998).

Myerson, D., Hackman, R.C., Nelson, J.A., Ward, D.C. & McDougall, J.K. Widespread presence of histologically occult cytomegalovirus. *Hum Pathol* 15, 430-9 (1984).

Nowlin, D.M., Cooper, N.R. & Compton, T. Expression of a human cytomegalovirus receptor correlates with infectibility of cells. *J Virol* 65, 3114-21(1991).

Ogawa, T., Asai, Y., Hashimoto, M. & Uchida, H. Bacterial fimbriae activate human peripheral blood monocytes utilizing TLR2, CD14 and CD1 1a/CD18 as cellular receptors. *Eur J Immunol* 32, 2543-50 (2002).

Perera, P.Y. et al. CD1 1b/CD18 acts in concert with CD14 and Toll-like receptor (TLR) 4 to elicit full lipopolysaccharide and taxol-inducible gene expression. *J Immunol* 166, 574-81 (2001).

Ramsay, M.E., Miller, B. & Peckham, C.S. Outcome of confirmed symptomatic congenital cytomegalovirus infection. *Arch Dis Child* 66, 1068-9 (1991).

Ruoslahti, E. RGD and other recognition sequences for integrmns. *Annu Rev Cell Dev Biol* 12, 697-7 15 (1996).

Sakai, T., Peyruchaud, O., Fassler, R. & Mosher, D.F. Restoration of beta1A integrins is required for lysophosphatidic acid-induced migration of beta 1 -null mouse fibroblastic cells. *J Biol Chem* 273, 19378-82 (1998).

Sanchez, V. et al. (2002) Viable human cytomegalovirus recombinant virus with an internal deletion of the 1E2 86 gene affects late stages of viral replication. *J Virol* 76 (6), 2973-2989.

Schoppel, K. et al. Antibodies specific for the antigenic domain 1 of glycoprotein B (gpULSS) of human cytomegalovirus bind to different substructures. *Virology* 216, 133-45 (1996).

Schwander, M. et al. Beta1 integrins regulate myoblast fusion and sarcomere assembly. *Dev Cell* 4, 673-85 (2003).

Sinzger, C. et al. Tropism of human cytomegalovirus for endothelial cells is determined by a post-entry step dependent on efficient translocation to the nucleus. *J Gen Virol* 81, 3021-35 (2000).

Spear, P.G. & Longnecker, R. Herpesvirus entry: an update .*J Virol* 77, 10179-85 (2003).

Stone, A.L., Kroeger, M. & Sang, Q.X. Structure-function analysis of the ADAM family of disintegrin-like and metalloproteinase-containing proteins (review). *J Protein Chem* 18, 447-65 (1999).

Superti, F. et al. (1987) Entry pathway of vesicular stomatitis virus into different host cells. *J Gen Virol* 68 (Pt 2), 387-399.

Triantafilou, K., Takada, Y. & Triantafilou, M. Mechanisms of integrin-mediated virus attachment and internalization process. *Crit Rev Immunol* 21, 311-22 (2001).

Tugizov, S.M., Berline, J.W. & Palefsky, J.M. Epstein-Barr virus infection of polarized tongue and nasopharyngeal epithelial cells. *Nat Med* 9, 307-14 (2003).

Valyi-Nagy, T., Bandi, Z., Boldogh, I. & Albrecht, T. Hydrolysis of inositol lipids: an early signal of human cytomegalovirus infection. *Arch Virol* 101, 199 207 (1988).

Wang, X., Huong, S.M., Chiu, M.L., Raab-Traub, N. & Huang, E.S. Epidermal growth factor receptor is a cellular receptor for human cytomegalovirus. *Nature* 424, 456-6 1 (2003).

\* cited by examiner

| Isolate | Protein ID | Acc. No. | gB Dis.-Like Sequence |
|---------|------------|----------|----------------------|
| N1 | CAB37015.1 | AJ236805 | RVCSMAQGIDLIRFERNIVC (SEQ. ID. 29) |
| N2 | CAB37016.1 | AJ236806 | RVCSMAQGIDLIRFERNIVC (SEQ. ID. 29) |
| N3 | CAB37015.1 | AJ236805 | RVCSMAQGIDLIRFERNIVC (SEQ. ID. 29) |
| N4 | CAB37015.1 | AJ236805 | RVCSMAQGIDLIRFERNIVC (SEQ. ID. 29) |
| N5 | CAB37015.1 | AJ236805 | RVCSMAQGIDLIRFERNIVC (SEQ. ID. 29) |
| N6 | CAB37015.1 | AJ236805 | RVCSMAQGIDLIRFERNIVC (SEQ. ID. 29) |
| N7 | CAB37017.1 | AJ236807 | RVCSMAQGIDLIRFERNIVC (SEQ. ID. 29) |
| N8 | CAB37015.1 | AJ236805 | RVCSMAQGIDLIRFERNIVC (SEQ. ID. 29) |
| N9 | CAB37015.1 | AJ236805 | RVCSMAQGIDLIRFERNIVC (SEQ. ID. 29) |
| N10 | CAB37015.1 | AJ236805 | RVCSMAQGIDLIRFERNIVC (SEQ. ID. 29) |
| N11 | CAB37021.1 | AJ236811 | RVCSMAQGIDLIRLERNIVC (SEQ. ID. 30) |
| N12 | CAB37022.1 | AJ236812 | RVCSLAQGIDLIRFERNIVC (SEQ. ID. 31) |
| N13 | CAB37025.1 | AJ236815 | RVCSMAQGIDLIRFERNIVC (SEQ. ID. 29) |
| N14 | CAB37026.1 | AJ236816 | RVCSMAQGIDLIRFERNIVC (SEQ. ID. 29) |
| N15 | CAB37027.1 | AJ236817 | RVCSMAQGIDLIRFERNIVC (SEQ. ID. 29) |
| N16 | CAB37028.1 | AJ236818 | RVCSMAQGIDLIRFERNIVC (SEQ. ID. 29) |
| N17 | CAB37029.1 | AJ236819 | RVCSMAQGIDLIRFERNIVC (SEQ. ID. 29) |
| N18 | CAB37030.1 | AJ236820 | RVCSMAQGIDLIRFERNIVC (SEQ. ID. 29) |
| N19 | CAB37031.1 | AJ236821 | RVCSMAQGIDLIRFERNIVC (SEQ. ID. 29) |
| N20 | CAB37032.1 | AJ236822 | RVCSMAQGIDLIRFERNIVC (SEQ. ID. 29) |
| N21 | CAB37033.1 | AJ236823 | RVCSMAQGIDLIRFERNIVC (SEQ. ID. 29) |
| N22 | CAB37038.1 | AJ236828 | RVCSMAQGIDLIRFDRNIVC (SEQ. ID. 32) |
| N23 | CAB37038.1 | AJ236828 | RVCSMAQGIDLIRFDRNIVC (SEQ. ID. 32) |
| N24 | CAB37038.1 | AJ236828 | RVCSMAQGIDLIRFDRNIVC (SEQ. ID. 32) |
| N25 | CAB37038.1 | AJ236828 | RVCSMAQGIDLIRFDRNIVC (SEQ. ID. 32) |
| N26 | CAB37038.1 | AJ236828 | RVCSMAQGIDLIRFDRNIVC (SEQ. ID. 32) |
| N27 | CAB37038.1 | AJ236828 | RVCSMAQGIDLIRFDRNIVC (SEQ. ID. 32) |
| N28 | CAB37039.1 | AJ236829 | RVCSMAQGIDLIRFDRNIVC (SEQ. ID. 32) |
| N29 | CAB37041.1 | AJ236831 | RVCSMAQGIDLIRFERNIVC (SEQ. ID. 29) |
| N30 | CAB37042.1 | AJ236832 | RVCSMAQGIDLIRFERNIVC (SEQ. ID. 29) |
| N31 | CAB37018.1 | AJ236808 | RVCSMAQGIDLIRFERNIVC (SEQ. ID. 29) |
| N32 | CAB37019.1 | AJ236809 | RVCSMAQGIDLIRFERNIVC (SEQ. ID. 29) |
| N33 | CAB37020.1 | AJ236810 | RVCSMAQGIDLIRFERNIVC (SEQ. ID. 29) |
| N34 | CAB37019.1 | AJ236809 | RVCSMAQGIDLIRFERNIVC (SEQ. ID. 29) |
| N35 | CAB37015.1 | AJ236805 | RVCSMAQGIDLIRFERNIVC (SEQ. ID. 29) |
| N36 | CAB37023.1 | AJ236813 | RVCSMAQGIDLIRLERNIIC (SEQ. ID. 33) |
| N37 | CAB37024.1 | AJ236814 | RVCSMAQGIDLIRFERNIIC (SEQ. ID. 34) |
| N38 | CAB37034.1 | AJ236824 | RVCSMAQGIDLIRFERNIVC (SEQ. ID. 29) |
| N39 | CAB37035.1 | AJ236825 | RVCSMAQGIDLIRFERNIVC (SEQ. ID. 29) |
| N40 | CAB37036.1 | AJ236826 | RVCSMAQGIDLIRFERNIVC (SEQ. ID. 29) |
| N41 | CAB37037.1 | AJ236827 | RVCSMAQGIDLIRFERNIVC (SEQ. ID. 29) |
| N42 | CAB37038.1 | AJ236828 | RVCSMAQGIDLIRFDRNIVC (SEQ. ID. 35) |
| N43 | CAB37040.1 | AJ236830 | RVCTMAQGIDLIRFDRNIVC (SEQ. ID. 36) |
| N44 | CAB37038.1 | AJ236828 | RVCSMAQGIDLIRFDRNIVC (SEQ. ID. 35) |
| AD169 | CAA35414.1 | CAA35414 | RVCSMAQGIDLIRFERNIIC (SEQ. ID. 34) |
| Towne | AAA45920.1 | AAA45920 | RVCSMAQGIDLIRFERNIVC (SEQ. ID. 29) |

FIG 1A

| | | | |
|---|---|---|---|
| ADAM Disintegrin Loop | Disintegrin-like | CR......CDL..F......C<br>** * ** * | |
| Herpesvirus | | R.C......DL..F.....C<br>** ** * | |
| BETA: | Human CMV | 92-RVCSMAQGTDLIRFERNIIC-111 | (SEQ. ID. NO: 37) |
| | Mouse CMV | 109-RVC-MSVSTDLVRFGKSIDC-127 | (SEQ. ID. NO: 38) |
| | Rhesus CMV | 67-RVCSMAQGTDLLRFEGNINC-86 | (SEQ. ID. NO: 39) |
| | Baboon CMV | 86-RVCSIAKGTDFLRFEQNIQC-105 | (SEQ. ID. NO: 40) |
| | Guinea Pig CMV | 82-RICSMSMGTDLVRFARTIQC-101 | (SEQ. ID. NO: 41) |
| | Porcine CMV | 81-RVCNMAVGTDLYRFDNYITC-100 | (SEQ. ID. NO: 42) |
| | HHV 6a | 39-RICSIAKGTDLMRFDRDISC-58 | (SEQ. ID. NO: 43) |
| | HHV 6b | 39-RICSIAKGTDLMRFDRDISC-58 | (SEQ. ID. NO: 44) |
| | HHV 7 | 36-RICSIATGTDLVRFDREVSC-55 | (SEQ. ID. NO: 45) |
| GAMMA: | EBV | 49-RVCELSSHGDLFRFSSDIQC-68 | (SEQ. ID. NO: 46) |
| | KSHV | 66-RVCSASITGELFRFNLEQTC-85 | (SEQ. ID. NO: 47) |
| | HVS | 43-RVCSASTTGELFRFDLDRTC-62 | (SEQ. ID. NO: 48) |
| | RRV | 62-RVCSASATGELFRFNLEKTC-81 | (SEQ. ID. NO: 49) |
| | MNV-68 | 68-RVCGVAATGETFRFDLDKTC-87 | (SEQ. ID. NO: 50) |
| ALPHA: | HSV-1 | 114-YVCPPPTGATVVQFEQPRRC-133 | (SEQ. ID. NO: 51) |
| | HSV-2 | 109-YVCPPPTGATVVQFEQPRRC-128 | (SEQ. ID. NO: 52) |
| | VZV | 57-YVCPPPTGSTIVRLEPTRTC-76 | (SEQ. ID. NO: 53) |

FIG 1B

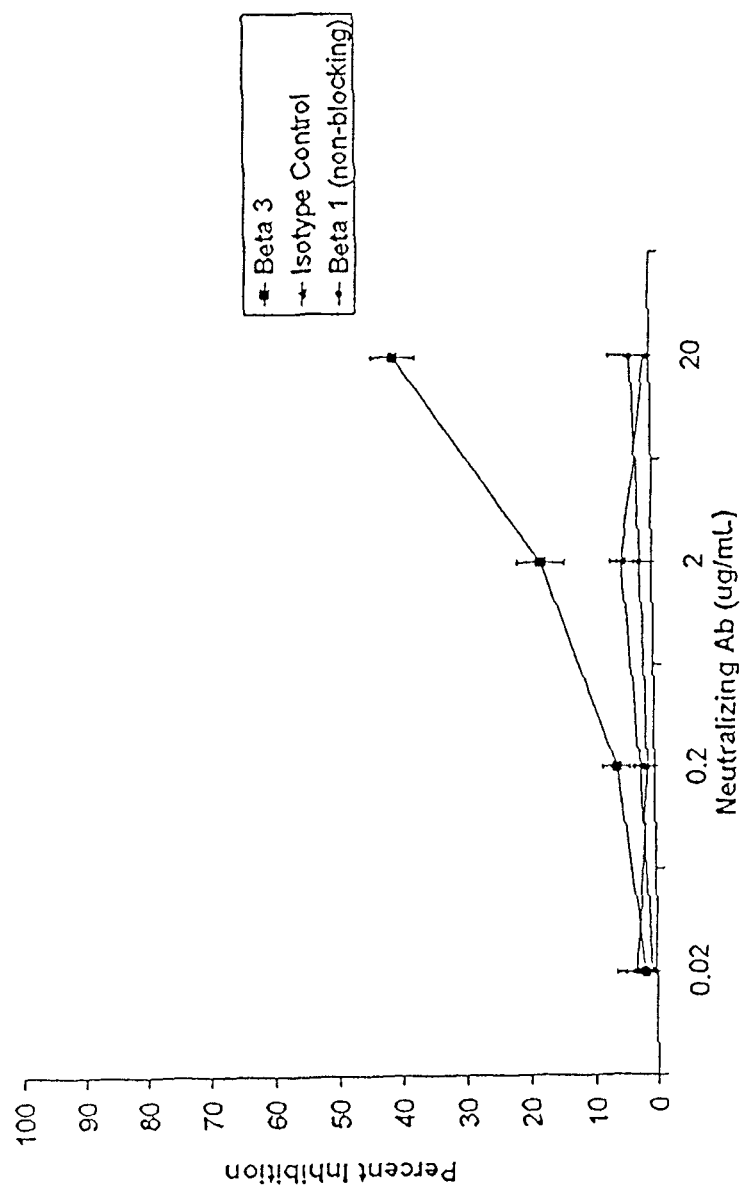

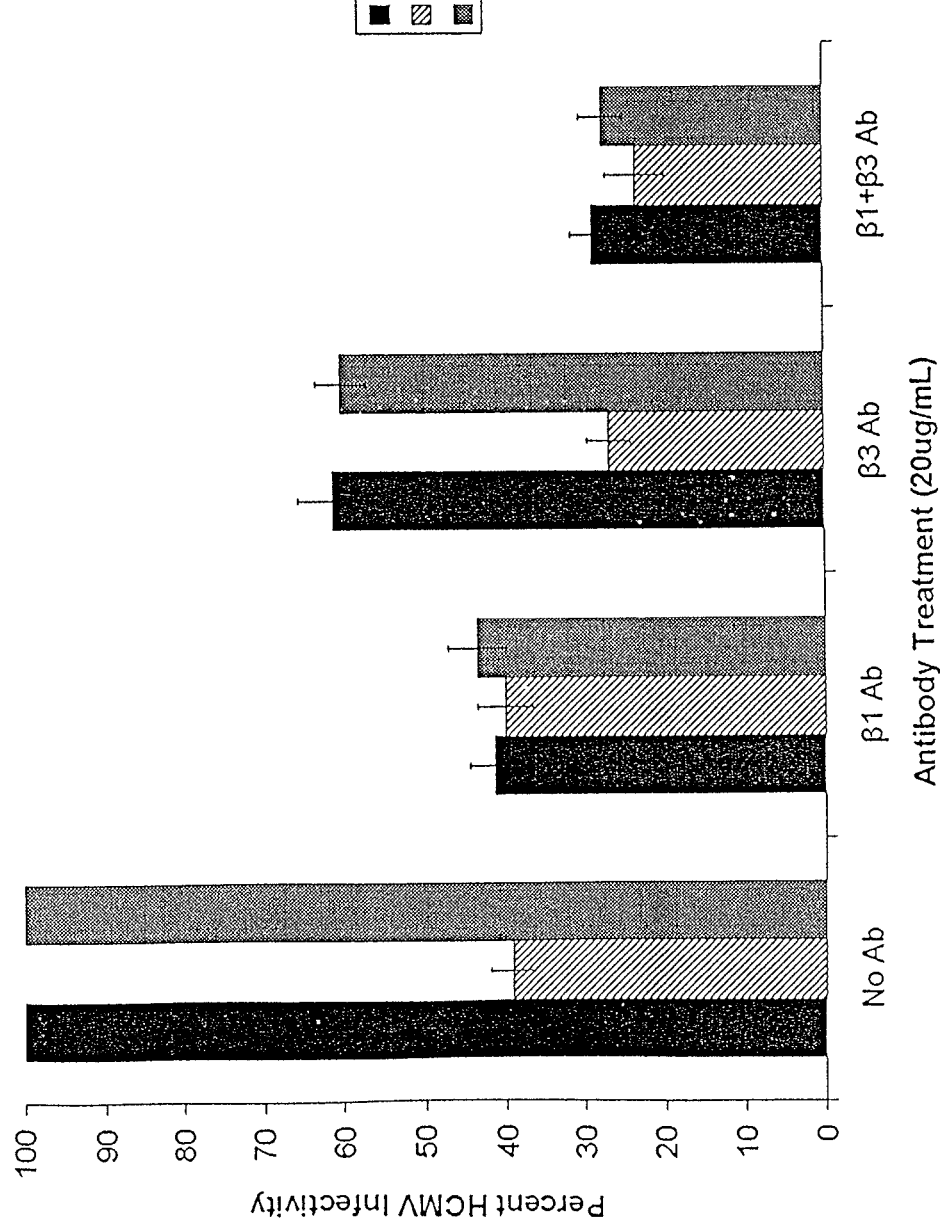

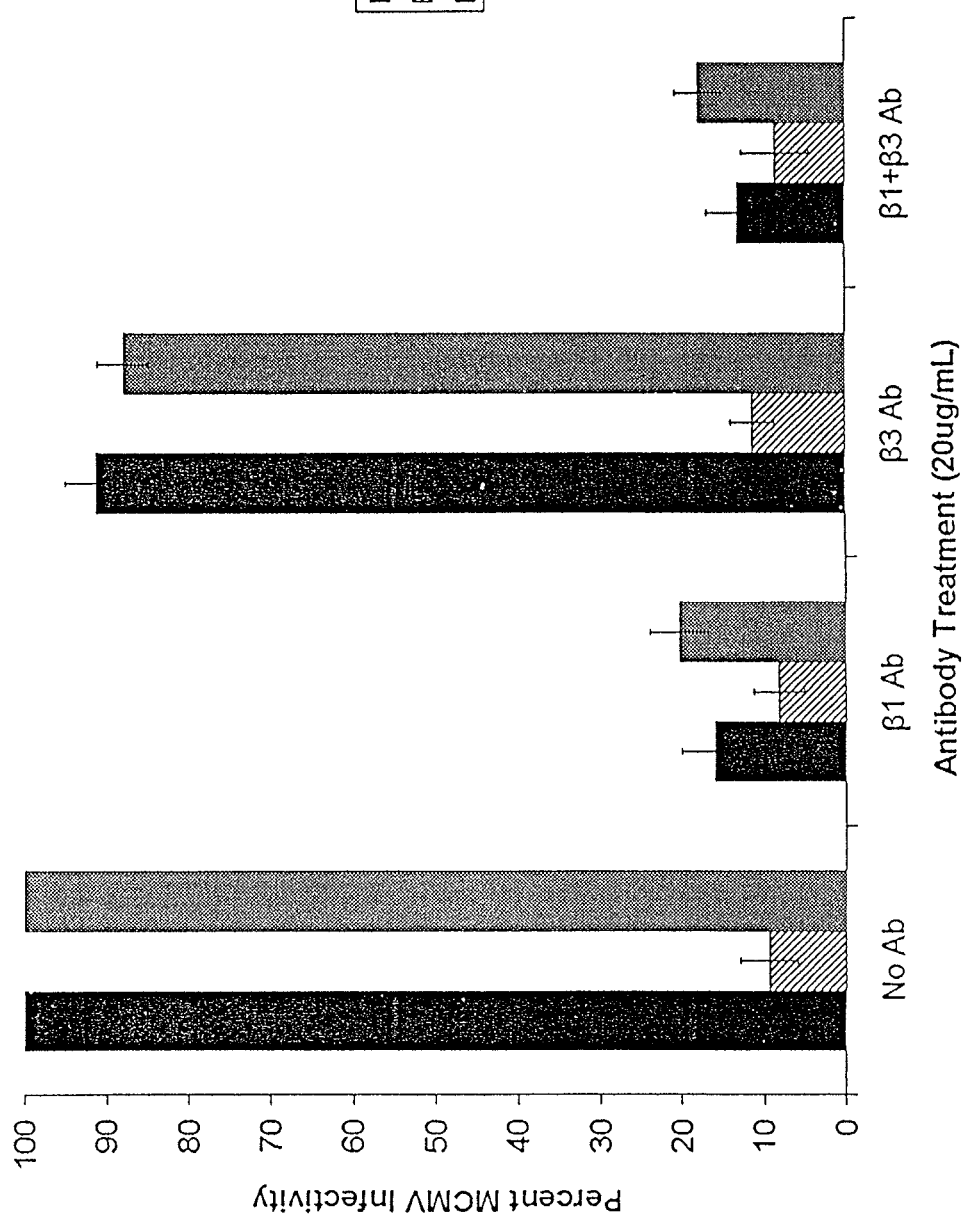

1   MESRIWCLVV  CVNLCIVCLG  AAVSSSSTSH  ATSSTHNGSH  TSRTTSAQTR  SVYSQHVTSS

61  EAVSHRANET  IYNTTLKYGD  VVGVNTTKYP  YRVCSMAQGT  DLIRFERNII  CTSMKPINED

121 LDEGIMVVYK  RNIVAHTFKV  RVYQKVLTFR  RSYAYIYTTY  LLGSNTEYVA  PPMWEIHHIN (SEQ. ID. NO: 54)

FIG 5

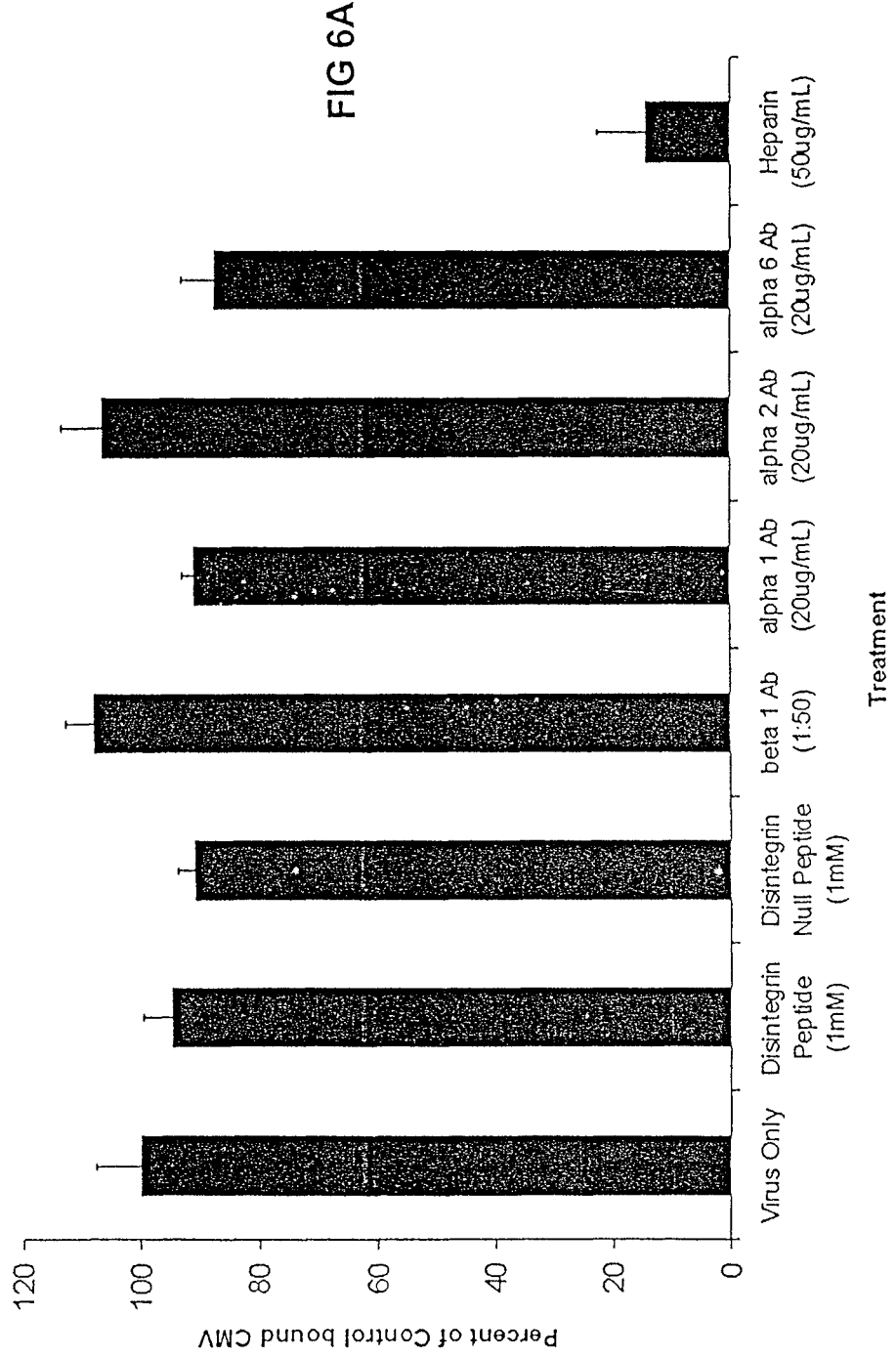

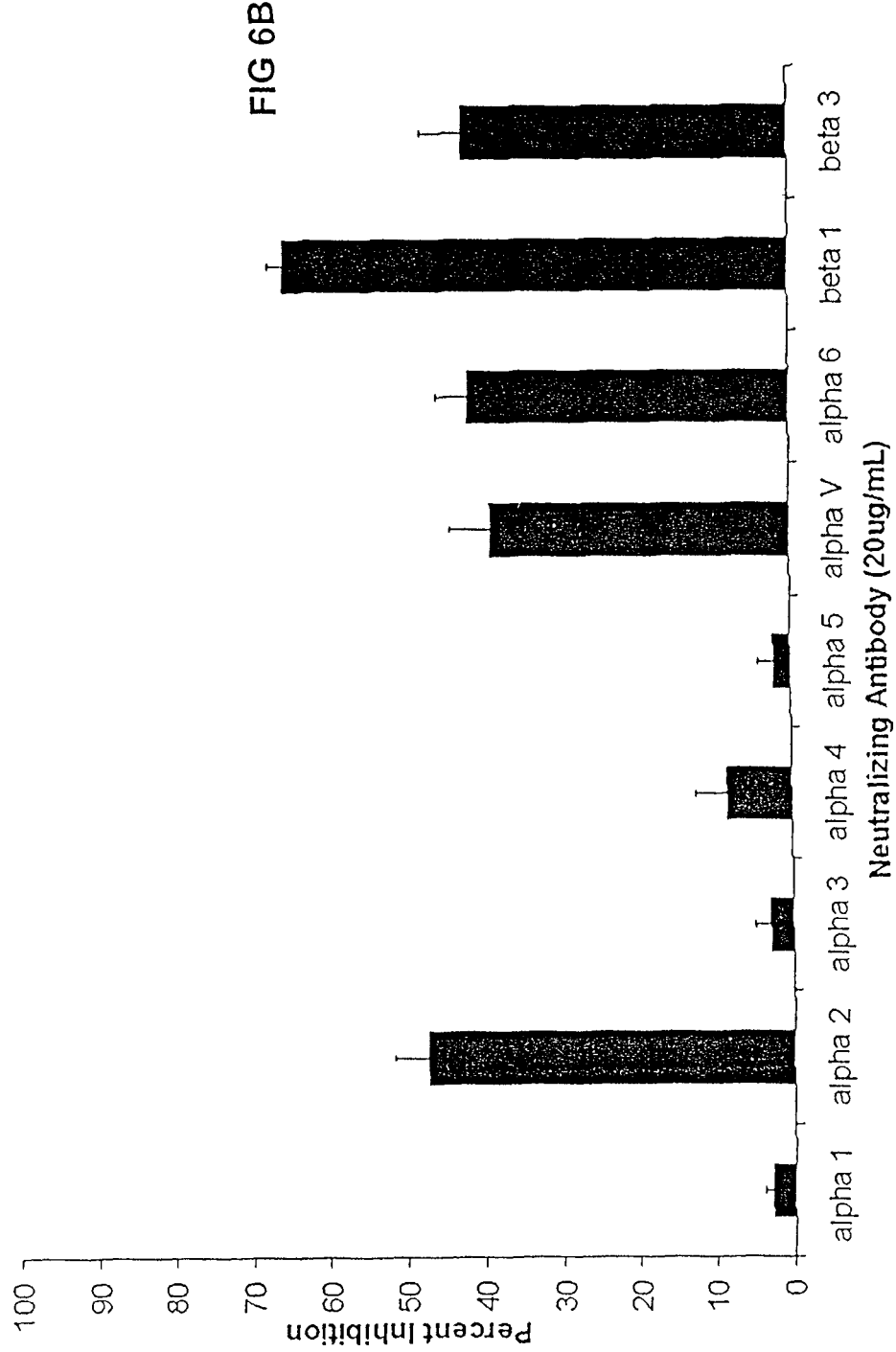

SEQUENCE LISTING

```
<160> NUMBER OF SEQ ID NOS: 54

<210> SEQ ID NO 1
<211> LENGTH: 17
<212> TYPE: PRT
<213> ORGANISM: Human cytomegalovirus
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
```

```
<222> LOCATION: (12)..(16)
<223> OTHER INFORMATION: Xaa can be any naturally occurring amino acid

<400> SEQUENCE: 1

Arg Xaa Xaa Xaa Xaa Xaa Asp Leu Xaa Xaa Phe Xaa Xaa Xaa Xaa Xaa
1               5                   10                  15

Cys

<210> SEQ ID NO 2
<211> LENGTH: 18
<212> TYPE: PRT
<213> ORGANISM: Human cytomegalovirus
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 2

Arg Xaa Xaa Xaa Xaa Xaa Xaa Asp Leu Xaa Xaa Phe Xaa Xaa Xaa Xaa
1               5                   10                  15

Xaa Cys

<210> SEQ ID NO 3
<211> LENGTH: 19
<212> TYPE: PRT
<213> ORGANISM: Human cytomegalovirus
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(18)
<223> OTHER INFORMATION: Xaa can be any naturally occurring amino acid

<400> SEQUENCE: 3

Arg Xaa Xaa Xaa Xaa Xaa Xaa Xaa Asp Leu Xaa Xaa Phe Xaa Xaa Xaa
1               5                   10                  15

Xaa Xaa Cys

<210> SEQ ID NO 4
<211> LENGTH: 20
<212> TYPE: PRT
<213> ORGANISM: Human cytomegalovirus
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(19)
<223> OTHER INFORMATION: Xaa can be any naturally occurring amino acid

<400> SEQUENCE: 4
```

```
Arg Xaa Xaa Xaa Xaa Xaa Xaa Xaa Asp Leu Xaa Xaa Phe Xaa Xaa
1               5                   10                  15

Xaa Xaa Xaa Cys
            20

<210> SEQ ID NO 5
<211> LENGTH: 20
<212> TYPE: PRT
<213> ORGANISM: Human cytomegalovirus

<400> SEQUENCE: 5

Arg Val Cys Ser Met Ala Gln Gly Thr Asp Leu Ile Arg Phe Glu Arg
1               5                   10                  15

Asn Ile Val Cys
            20

<210> SEQ ID NO 6
<211> LENGTH: 20
<212> TYPE: PRT
<213> ORGANISM: Epstein-Barr virus

<400> SEQUENCE: 6

Arg Val Cys Glu Leu Ser Ser His Gly Asp Leu Phe Arg Phe Ser Ser
1               5                   10                  15

Asp Ile Gln Cys
            20

<210> SEQ ID NO 7
<211> LENGTH: 20
<212> TYPE: PRT
<213> ORGANISM: Kaposi's sarcoma-associated herpesvirus

<400> SEQUENCE: 7

Arg Val Cys Ser Ala Ser Ile Thr Gly Glu Leu Phe Arg Phe Asn Leu
1               5                   10                  15

Glu Gln Thr Cys
            20

<210> SEQ ID NO 8
<211> LENGTH: 20
<212> TYPE: PRT
<213> ORGANISM: Human cytomegalovirus

<400> SEQUENCE: 8

Arg Val Cys Ser Met Ala Gln Gly Thr Asp Leu Ile Arg Phe Glu Arg
1               5                   10                  15

Asn Ile Ile Cys
            20

<210> SEQ ID NO 9
<211> LENGTH: 20
<212> TYPE: PRT
<213> ORGANISM: Human cytomegalovirus

<400> SEQUENCE: 9

Ala Val Cys Ser Met Ala Gly Gly Thr Ala Ala Ile Arg Ala Glu Arg
1               5                   10                  15

Asn Ile Ile Cys
            20

<210> SEQ ID NO 10
<211> LENGTH: 7
<212> TYPE: PRT
```

```
<213> ORGANISM: Artificial
<220> FEATURE:
<223> OTHER INFORMATION: Integrin recognition motif

<400> SEQUENCE: 10

Arg Arg Glu Thr Ala Trp Ala
1               5

<210> SEQ ID NO 11
<211> LENGTH: 4
<212> TYPE: PRT
<213> ORGANISM: Artificial
<220> FEATURE:
<223> OTHER INFORMATION: Integrin recognition motif

<400> SEQUENCE: 11

Arg Glu Asp Val
1

<210> SEQ ID NO 12
<211> LENGTH: 4
<212> TYPE: PRT
<213> ORGANISM: Artificial
<220> FEATURE:
<223> OTHER INFORMATION: Integrin recognition motif

<400> SEQUENCE: 12

Ser Asp Gly Arg
1

<210> SEQ ID NO 13
<211> LENGTH: 5
<212> TYPE: PRT
<213> ORGANISM: Artificial
<220> FEATURE:
<223> OTHER INFORMATION: Integrin recognition motif

<400> SEQUENCE: 13

Tyr Ile Gly Ser Arg
1               5

<210> SEQ ID NO 14
<211> LENGTH: 5
<212> TYPE: PRT
<213> ORGANISM: Artificial
<220> FEATURE:
<223> OTHER INFORMATION: Integrin recognition motif

<400> SEQUENCE: 14

Tyr Ile Gly Ser Glu
1               5

<210> SEQ ID NO 15
<211> LENGTH: 4
<212> TYPE: PRT
<213> ORGANISM: Artificial
<220> FEATURE:
<223> OTHER INFORMATION: Integrin recognition motif

<400> SEQUENCE: 15

Arg Gly Glu Ser
1

<210> SEQ ID NO 16
<211> LENGTH: 5
<212> TYPE: PRT
<213> ORGANISM: Artificial
<220> FEATURE:
```

-continued

<223> OTHER INFORMATION: Integrin recognition motif

<400> SEQUENCE: 16

Arg Ser Gly Ile Tyr
1               5

<210> SEQ ID NO 17
<211> LENGTH: 4
<212> TYPE: PRT
<213> ORGANISM: Artificial
<220> FEATURE:
<223> OTHER INFORMATION: Integrin recognition motif

<400> SEQUENCE: 17

Arg Ser Gly Asp
1

<210> SEQ ID NO 18
<211> LENGTH: 4
<212> TYPE: PRT
<213> ORGANISM: Artificial
<220> FEATURE:
<223> OTHER INFORMATION: Integrin recognition motif

<400> SEQUENCE: 18

Asp Arg Asp Glu
1

<210> SEQ ID NO 19
<211> LENGTH: 4
<212> TYPE: PRT
<213> ORGANISM: Artificial
<220> FEATURE:
<223> OTHER INFORMATION: Integrin recognition motif

<400> SEQUENCE: 19

Ser Arg Tyr Asp
1

<210> SEQ ID NO 20
<211> LENGTH: 12
<212> TYPE: PRT
<213> ORGANISM: Unknown
<220> FEATURE:
<223> OTHER INFORMATION: Integrin-binding disintegrin-like consensus
      sequence from ADAMS protein family
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 20

Arg Xaa Xaa Xaa Xaa Xaa Xaa Asp Leu Xaa Xaa Phe
1               5                   10

<210> SEQ ID NO 21
<211> LENGTH: 13
<212> TYPE: PRT
<213> ORGANISM: Unknown
<220> FEATURE:
<223> OTHER INFORMATION: Integrin-binding disintegrin-like consensus
      sequence from ADAMS protein family
<220> FEATURE:
<221> NAME/KEY: misc_feature
<222> LOCATION: (2)..(8)
<223> OTHER INFORMATION: Xaa can be any naturally occurring amino acid

```
<220> FEATURE:
<221> NAME/KEY: misc_feature
<222> LOCATION: (11)..(12)
<223> OTHER INFORMATION: Xaa can be any naturally occurring amino acid

<400> SEQUENCE: 21

Arg Xaa Xaa Xaa Xaa Xaa Xaa Xaa Asp Leu Xaa Xaa Phe
1               5                   10

<210> SEQ ID NO 22
<211> LENGTH: 14
<212> TYPE: PRT
<213> ORGANISM: Unknown
<220> FEATURE:
<223> OTHER INFORMATION: Integrin-binding disintegrin-like consensus
      sequence from ADAMS protein family
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 22

Arg Xaa Xaa Xaa Xaa Xaa Xaa Xaa Xaa Asp Leu Xaa Xaa Phe
1               5                   10

<210> SEQ ID NO 23
<211> LENGTH: 11
<212> TYPE: PRT
<213> ORGANISM: Unknown
<220> FEATURE:
<223> OTHER INFORMATION: Disintegrin-like domain from ADAMS protein
      family
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 23

Arg Xaa Xaa Xaa Xaa Xaa Asp Leu Xaa Xaa Phe
1               5                   10

<210> SEQ ID NO 24
<211> LENGTH: 12
<212> TYPE: PRT
<213> ORGANISM: Unknown
<220> FEATURE:
<223> OTHER INFORMATION: Disintegrin-like domain from ADAMS protein
      family
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 24

Arg Xaa Xaa Xaa Xaa Xaa Xaa Asp Leu Xaa Xaa Phe
1               5                   10

<210> SEQ ID NO 25
<211> LENGTH: 13
<212> TYPE: PRT
```

```
<213> ORGANISM: Unknown
<220> FEATURE:
<223> OTHER INFORMATION: Disintegrin-like domain from ADAMS protein
      family
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 25

Arg Xaa Xaa Xaa Xaa Xaa Xaa Xaa Asp Leu Xaa Xaa Phe
1               5                   10

<210> SEQ ID NO 26
<211> LENGTH: 11
<212> TYPE: PRT
<213> ORGANISM: Unknown
<220> FEATURE:
<223> OTHER INFORMATION: Disintegrin-like domain from ADAMS protein
      family
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 26

Arg Xaa Xaa Xaa Xaa Xaa Asp Leu Xaa Xaa Leu
1               5                   10

<210> SEQ ID NO 27
<211> LENGTH: 12
<212> TYPE: PRT
<213> ORGANISM: Unknown
<220> FEATURE:
<223> OTHER INFORMATION: Disintegrin-like domain from ADAMS protein
      family
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 27

Arg Xaa Xaa Xaa Xaa Xaa Xaa Asp Leu Xaa Xaa Leu
1               5                   10

<210> SEQ ID NO 28
<211> LENGTH: 13
<212> TYPE: PRT
<213> ORGANISM: Unknown
<220> FEATURE:
<223> OTHER INFORMATION: Disintegrin-like domain from ADAMS protein
      family
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 28
```

```
Arg Xaa Xaa Xaa Xaa Xaa Xaa Asp Leu Xaa Xaa Leu
1               5                   10
```

<210> SEQ ID NO 29
<211> LENGTH: 20
<212> TYPE: PRT
<213> ORGANISM: Human cytomegalovirus

<400> SEQUENCE: 29

```
Arg Val Cys Ser Met Ala Gln Gly Ile Asp Leu Ile Arg Phe Glu Arg
1               5                   10                  15

Asn Ile Val Cys
            20
```

<210> SEQ ID NO 30
<211> LENGTH: 20
<212> TYPE: PRT
<213> ORGANISM: Human cytomegalovirus

<400> SEQUENCE: 30

```
Arg Val Cys Ser Met Ala Gln Gly Ile Asp Leu Ile Arg Leu Glu Arg
1               5                   10                  15

Asn Ile Val Cys
            20
```

<210> SEQ ID NO 31
<211> LENGTH: 20
<212> TYPE: PRT
<213> ORGANISM: Human cytomegalovirus

<400> SEQUENCE: 31

```
Arg Val Cys Ser Leu Ala Gln Gly Ile Asp Leu Ile Arg Phe Glu Arg
1               5                   10                  15

Asn Ile Val Cys
            20
```

<210> SEQ ID NO 32
<211> LENGTH: 20
<212> TYPE: PRT
<213> ORGANISM: Human cytomegalovirus

<400> SEQUENCE: 32

```
Arg Val Cys Ser Met Ala Gln Gly Ile Asp Leu Ile Arg Phe Asp Arg
1               5                   10                  15

Asn Ile Val Cys
            20
```

<210> SEQ ID NO 33
<211> LENGTH: 20
<212> TYPE: PRT
<213> ORGANISM: Human cytomegalovirus

<400> SEQUENCE: 33

```
Arg Val Cys Ser Met Ala Gln Gly Ile Asp Leu Ile Arg Leu Glu Arg
1               5                   10                  15

Asn Ile Ile Cys
            20
```

<210> SEQ ID NO 34
<211> LENGTH: 20
<212> TYPE: PRT
<213> ORGANISM: Human cytomegalovirus -continued

```
<400> SEQUENCE: 34

Arg Val Cys Ser Met Ala Gln Gly Ile Asp Leu Ile Arg Phe Glu Arg
1               5                   10                  15

Asn Ile Ile Cys
            20

<210> SEQ ID NO 35
<211> LENGTH: 20
<212> TYPE: PRT
<213> ORGANISM: Human cytomegalovirus

<400> SEQUENCE: 35

Arg Val Cys Ser Met Ala Gln Gly Ile Asp Leu Ile Arg Phe Asp Arg
1               5                   10                  15

Asn Ile Val Cys
            20

<210> SEQ ID NO 36
<211> LENGTH: 20
<212> TYPE: PRT
<213> ORGANISM: Human cytomegalovirus

<400> SEQUENCE: 36

Arg Val Cys Thr Met Ala Gln Gly Ile Asp Leu Ile Arg Phe Asp Arg
1               5                   10                  15

Asn Ile Val Cys
            20

<210> SEQ ID NO 37
<211> LENGTH: 20
<212> TYPE: PRT
<213> ORGANISM: Human cytomegalovirus

<400> SEQUENCE: 37

Arg Val Cys Ser Met Ala Gln Gly Thr Asp Leu Ile Arg Phe Glu Arg
1               5                   10                  15

Asn Ile Ile Cys
            20

<210> SEQ ID NO 38
<211> LENGTH: 19
<212> TYPE: PRT
<213> ORGANISM: Murine cytomegalovirus

<400> SEQUENCE: 38

Arg Val Cys Met Ser Val Ser Thr Asp Leu Val Arg Phe Gly Lys Ser
1               5                   10                  15

Ile Asp Cys

<210> SEQ ID NO 39
<211> LENGTH: 20
<212> TYPE: PRT
<213> ORGANISM: Rhesus cytomegalovirus

<400> SEQUENCE: 39

Arg Val Cys Ser Met Ala Gln Gly Thr Asp Leu Leu Arg Phe Glu Gly
1               5                   10                  15

Asn Ile Asn Cys
            20

<210> SEQ ID NO 40
<211> LENGTH: 20
```

```
<212> TYPE: PRT
<213> ORGANISM: Baboon cytomegalovirus

<400> SEQUENCE: 40

Arg Val Cys Ser Ile Ala Lys Gly Thr Asp Phe Leu Arg Phe Glu Gln
1               5                   10                  15

Asn Ile Gln Cys
            20

<210> SEQ ID NO 41
<211> LENGTH: 20
<212> TYPE: PRT
<213> ORGANISM: Guinea pig cytomegalovirus

<400> SEQUENCE: 41

Arg Ile Cys Ser Met Ser Met Gly Thr Asp Leu Val Arg Phe Ala Arg
1               5                   10                  15

Thr Ile Gln Cys
            20

<210> SEQ ID NO 42
<211> LENGTH: 20
<212> TYPE: PRT
<213> ORGANISM: Porcine cytomegalovirus

<400> SEQUENCE: 42

Arg Val Cys Asn Met Ala Val Gly Thr Asp Leu Tyr Arg Phe Asp Asn
1               5                   10                  15

Tyr Ile Thr Cys
            20

<210> SEQ ID NO 43
<211> LENGTH: 20
<212> TYPE: PRT
<213> ORGANISM: Human herpesvirus 6A

<400> SEQUENCE: 43

Arg Ile Cys Ser Ile Ala Lys Gly Thr Asp Leu Met Arg Phe Asp Arg
1               5                   10                  15

Asp Ile Ser Cys
            20

<210> SEQ ID NO 44
<211> LENGTH: 20
<212> TYPE: PRT
<213> ORGANISM: Human herpesvirus 6B

<400> SEQUENCE: 44

Arg Ile Cys Ser Ile Ala Lys Gly Thr Asp Leu Met Arg Phe Asp Arg
1               5                   10                  15

Asp Ile Ser Cys
            20

<210> SEQ ID NO 45
<211> LENGTH: 20
<212> TYPE: PRT
<213> ORGANISM: Human herpesvirus 7

<400> SEQUENCE: 45

Arg Ile Cys Ser Ile Ala Thr Gly Thr Asp Leu Val Arg Phe Asp Arg
1               5                   10                  15

Glu Val Ser Cys
            20
```

-continued

<210> SEQ ID NO 46
<211> LENGTH: 20
<212> TYPE: PRT
<213> ORGANISM: Epstein-Barr virus

<400> SEQUENCE: 46

Arg Val Cys Glu Leu Ser Ser His Gly Asp Leu Phe Arg Phe Ser Ser
1               5                   10                  15

Asp Ile Gln Cys
            20

<210> SEQ ID NO 47
<211> LENGTH: 20
<212> TYPE: PRT
<213> ORGANISM: Kaposi's sarcoma-related virus

<400> SEQUENCE: 47

Arg Val Cys Ser Ala Ser Ile Thr Gly Glu Leu Phe Arg Phe Asn Leu
1               5                   10                  15

Glu Gln Thr Cys
            20

<210> SEQ ID NO 48
<211> LENGTH: 20
<212> TYPE: PRT
<213> ORGANISM: human gamma-2 herpesvirus

<400> SEQUENCE: 48

Arg Val Cys Ser Ala Ser Thr Thr Gly Glu Leu Phe Arg Phe Asp Leu
1               5                   10                  15

Asp Arg Thr Cys
            20

<210> SEQ ID NO 49
<211> LENGTH: 20
<212> TYPE: PRT
<213> ORGANISM: Ross River virus

<400> SEQUENCE: 49

Arg Val Cys Ser Ala Ser Ala Thr Gly Glu Leu Phe Arg Phe Asn Leu
1               5                   10                  15

Glu Lys Thr Cys
            20

<210> SEQ ID NO 50
<211> LENGTH: 20
<212> TYPE: PRT
<213> ORGANISM: Murine norovirus

<400> SEQUENCE: 50

Arg Val Cys Gly Val Ala Ala Thr Gly Glu Thr Phe Arg Phe Asp Leu
1               5                   10                  15

Asp Lys Thr Cys
            20

<210> SEQ ID NO 51
<211> LENGTH: 20
<212> TYPE: PRT
<213> ORGANISM: herpes simplex virus 1

<400> SEQUENCE: 51

Tyr Val Cys Pro Pro Pro Thr Gly Ala Thr Val Val Gln Phe Glu Gln

```
                1               5                   10                  15
Pro Arg Arg Cys
            20

<210> SEQ ID NO 52
<211> LENGTH: 20
<212> TYPE: PRT
<213> ORGANISM: herpes simplex virus 2

<400> SEQUENCE: 52

Tyr Val Cys Pro Pro Thr Gly Ala Thr Val Val Gln Phe Glu Gln
1               5                   10                  15

Pro Arg Arg Cys
            20

<210> SEQ ID NO 53
<211> LENGTH: 20
<212> TYPE: PRT
<213> ORGANISM: Varicella zoster virus

<400> SEQUENCE: 53

Tyr Val Cys Pro Pro Thr Gly Ser Thr Ile Val Arg Leu Glu Pro
1               5                   10                  15

Thr Arg Thr Cys
            20

<210> SEQ ID NO 54
<211> LENGTH: 180
<212> TYPE: PRT
<213> ORGANISM: Artificial
<220> FEATURE:
<223> OTHER INFORMATION: Cloned gD-DLD diintegrin-like peptide and
      flanking sequences

<400> SEQUENCE: 54

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn
            180
```

CYTOMEGALOVIRUS DISINTEGRIN-LIKE PEPTIDES

CROSS-REFERENCE TO RELATED APPLICATIONS

This is a divisional of application Ser. No. 11/127,601, filed May 12, 2005 (now U.S. Pat. No. 7,491,490, issued Feb. 17, 2009), which claims priority to provisional application Ser. No. 60/570,260, filed May 12, 2004, the entire content of which is incorporated herein.

STATEMENT REGARDING FEDERAL FUNDING

The invention was made with United States government support awarded by the following agency: NIH AI034998. The United States government has certain rights in this invention.

BACKGROUND OF THE INVENTION

Human cytomegalovirus (HCMV) is a member of the medically significant Herpesviridae family of viruses, a family divided into three subfamilies: alpha-, beta- and gamma-herpesviruses. Herpesviruses establish a life-long relationship with their hosts and can manifest disease in an opportunistic manner. HCMV is the most common viral cause of congenital birth defects and is responsible for significant morbidity and mortality in immunocompromised patients, including AIDS patients and organ transplant recipients.[1,2] A notable feature of HCMV pathogenesis is its exceptionally broad tissue tropism. HCMV is capable of manifesting disease in most organ systems and tissue types, which directly correlates with its ability to infect fibroblasts, endothelial cells, epithelial cells, monocytes/macrophages, smooth muscle cells, stromal cells, neuronal cells, neutrophils, and hepatocytes.[3-5] In vitro entry into target cells is equally promiscuous, as HCMV is able to bind, penetrate and initiate replication in all tested vertebrate cell types.[6] Recently, epidermal growth factor receptor (EGFR) was identified as a cellular receptor for HCMV. Expression of EGFR was found to correlate with the ability of the virus to initiate gene expression.[7] However, EGFR is not expressed on several HCMV-permissive cells, such as hematopoetic cell types. Therefore other receptors that HCMV can exploit to gain entry into various cell types must exist.

Many of the physiological consequences associated with HCMV infection are consistent with activation of cellular integrins. Host cells respond to HCMV infection by activating numerous signal transduction pathways including initiating $Ca^{++}$ influx at the cell membrane, as well as activating phospolipases C and A2, mitogen-activated protein kinase (MAP kinase), p38, NF-KB and SP-1.[8,9] HCMV also induces a distinct cytopathology, with cells rounding 30-60 minutes post-viral challenge corresponding to the entry event and then once again 24 hours post-infection.[10]

In recent years, cellular integrins have emerged as entry receptors for a broad range of pathogens including pathogenic plant spores, bacteria and several families of viruses. Integrins have been shown to mediate both the initial attachment of virions to the cell surface, as well as to facilitate the "post-attachment" or internalization entry step.[11] Integrins are expressed on the cell surface as a noncovalently linked heterodimer consisting of a α and β subunit, which conveys specificity in cell-cell adhesion, cell-extracellular matrix (ECM) adhesion, immune cell recruitment, extravasation and signaling.[12,13] Although each specific integrin heterodimer has a specific set of ligands, many integrin heterodimers have overlapping ligand-binding capabilities, a characteristic that many pathogens have evolved to exploit; most viruses that utilize integrins as receptors are capable of interacting with several integrin heterodimers.

There are several known integrin recognition motifs. The most common of these involves the amino acid sequence RGD. There are, however, a number of RGD-independent integrin recognition motifs. These include motifs found in certain extracellular matrix proteins and the disintegrin-like domain found in the family of proteins known as ADAMS (A Disintegrin And a Metalloprotease).[14] From the 30 known members of the ADAM family, a disintegrin-like domain consensus and minimum integrin recognition motif has been identified ($RX_{5-7}DLXXF/L$) (SEQ. ID. NOS: 23-28).[14,15]

Researchers have established that viral glycoprotein B (gB) is a protein that is required for virus entry and fusion throughout the Herpesviridae family. Glycoprotein B is a critical member of the conserved basic fusion machinery.[16] During virus entry, HCMV induces cellular morphological changes and signaling cascades consistent with engagement of cellular integrins; however, HCMV structural proteins do not possess the widely used RGD integrin binding motif. Thus, it would be desirable to identify a conserved receptor-binding domain within the Herpesviridae family that can be used to inhibit viral entry into host cells.

BRIEF SUMMARY OF THE INVENTION

The present invention is directed to methods and compositions of matter for inhibiting the entry of viruses in general, and herpesviruses in particular, into host cells. Through antibody blocking and integrin-knockout cell experiments, it has been determined that integrins are utilized as CMV entry receptors to facilitate viral entry into a host. The present inventors have also identified the presence of an integrin-binding gB disintegrin-like domain that is highly conserved among herpesviruses. It has been determined that these conserved viral gB disintegrin-like domains are capable of engaging cellular integrins, thereby facilitating fusion of the virion to the host cell and ultimate entry of the virion into the host cell. Thus, the present invention provides methods and compositions for inhibiting, interfering with, or otherwise blocking the interaction between the gB disintegrin-like domain of a virus and the integrins of a putative host cell, thereby inhibiting and/or preventing entry of the virus into the host cell.

In one aspect the invention provides a method for inhibiting viral entry into an animal host cell by administering to the host cell an agent capable of interfering with integrin engagement of HCMV and thereby inhibiting viral internalization into the host cell.

In another aspect the invention provides an anti-viral agent comprising an integrin binding gB disintegrin-like peptide or peptidomimetic capable of blocking integrin engagement of HCMV and thereby inhibiting viral internalization into the host cell.

In yet another aspect the invention provides an antibody produced against an integrin binding gB disintegrin-like peptide, wherein the antibody is capable of binding a viral gB disintegrin-like domain, thereby inhibiting viral internalization into a host cell by interfering with virus-integrin engagement.

More specifically, one aspect of the invention is directed to a method of inhibiting viral infection of an animal host cell. The method comprises administering to the host cell (either in vitro, in vivo, or ex vivo) an antiviral-effective amount of a purified, integrin-binding gB disintegin-like peptide or a purified antibody that binds specifically to an integrin-binding, gB disintegrin-like peptide.

In the preferred embodiment, the purified, integrin-binding gB disintegrin-like peptide comprises an amino acid consensus sequence $RX_{5-8}DLXXFX_5C$ (SEQ. ID. NOS: 1-4) or an amino acid sequence at least 80% homologous thereto. In another preferred embodiment, the purified, integrin-binding gB disintegrin-like peptide comprises an amino acid sequence RVCSMAQGTDLIRFERNIVC (SEQ. ID. NO: 5) or an amino acid sequence at least 80% homologous thereto. Likewise, when the active agent is an antibody, it is preferred that the purified antibody binds selectively to SEQ. ID. NOS: 1-5 or a sequence at least 80% homologous to one of these two sequences. Additionally, the purified antibody may bind selectively to an integrin-binding, gB disintegrin-like peptide comprising residues 91-111 of glycoprotein B of human cytomegalovirus.

The method disclosed is for inhibiting the viral infection of animal cells. More particularly, the method is for inhibiting infection of animal cells by viruses of the family Herpesviridae (V.C. 31), more particularly still for inhibiting infection by viruses of the family Herpesviridae and sub-family Beta herpesvirinae (V.C. 31.2), and more particularly even still for inhibiting infection by viruses of the family Herpesviridae, sub-family Beta herpesvirinae, genus Cytomegalovirus (V.C. 31.2.1) into the host cell. For more information on the taxonomy of viruses, see the International Committee on Taxonomy of Viruses Database (ICTVdB), jointly maintained by the National Center for Biotechnology Information (Bethesda, Md.) and Columbia University (New York, N.Y.).

The method may utilize purified monoclonal antibodies or purified polyclonal antibodies.

The invention is also directed to pharmaceutical compositions comprising an antiviral-effective amount of a purified, integrin-binding gB disintegrin-like peptide as described above, or a purified antibody that binds specifically to an integrin-binding, gB disintegrin-like peptide.

The invention is further directed to a purified polypeptide comprising SEQ. ID. NOS: 1-5 or an amino acid sequence having at least 80% homology to SEQ. ID. NOS: 1-5.

The invention is also directed to a purified antibody that binds specifically to an integrin-binding, gB disintegrin-like peptide. In the preferred embodiment, the antibody binds selectively to an integrin-binding, gB disintegrin-like peptide comprising SEQ. ID. NOS: 1-5 or a sequence at least 80% homologous thereto. The antibody may be monoclonal or polyclonal. It is also preferred that the antibody inhibits internalization of viruses of the family Herpesviridae into host cells, more preferred still that the antibody inhibits internalization of viruses of the family Herpesviridae and sub-family Beta herpesvirinae into host cells, and most preferred that the antibody inhibits internalization of viruses of the family Herpesviridae, sub-family Beta herpesvirinae, and genus Cytomegalovirus into the host cells.

Other objects, advantages and features of the present invention will become apparent from the following specification taken in conjunction with the accompanying drawings.

BRIEF DESCRIPTION OF THE DRAWINGS

FIG. 1A is a sequence alignment showing the conservation of the gB disintegrin-like domain in various HCMV clinical isolate protein sequences deposited in the GenBank database (operated by the National Center for Biotechnology Information, Bethesda, Md.). The conserved herpesvirus gB disintegin-like consensus sequence is in bold, underline type. Conserved β-herpesvirus residues are in bold type. Non-conserved residues are in italics.

FIG. 1B is a sequence alignment showing the conservation of the gB disintegrin-like domain in various herpesviruses. The conserved herpesvirus gB disintegin-like consensus sequence is in bold, underline type. Conserved β-herpesvirus residues are in bold type.

FIG. 3B is a graph showing that integrin-neutralizing antibodies inhibit HCMV infectivity in a dose-dependent fashion. The graph depicts the results of treating NHDFs with neutralizing monoclonal antibodies to the β3 integrin (which inhibited CMV infection in a dose-dependent fashion), as well as an isotype control and treating the cells with a β1 integrin subunit non-neutralizing antibody (neither of which showed inhibitory activity).

FIG. 4A is a histogram showing the treatment of GD25, GD25β1 and NHDF cells with or without β1, β3, and β1+β3 antibodies, followed by HCMV infection. The histogram shows that cells that are null for β1 integrin exhibit decreased HCMV entry.

FIG. 4B is a histogram showing the treatment of GD25, GD25β1 and 3T3 cells with or without β1, β3, β1+β3 antibodies followed by MCMV infection. The histogram shows that cells that are null for β1 integrin exhibit decreased MCMV entry.

FIG. 5 depicts the $gB_{DLD}$ fragment in the context of the native N-terminus of HCMV glycoprotein B (gB). The underlined sequence is the $gB_{DLD}$ proper. The bold, underlined sequence is the consensus integrin recognition motif and the sequence of the original disintegrin-like synthetic peptide.

FIG. 6A is a histogram depicting the effects of integrin-blocking treatments on HCMV binding and entry into NHDF cells.

FIG. 6B is a histogram depicting viral payloads as measured by pp65 localization in NHFD cells after the cells were treated with various integrin-blocking agents and then infected with HCMV.

DETAILED DESCRIPTION OF THE INVENTION

Figure 2A:
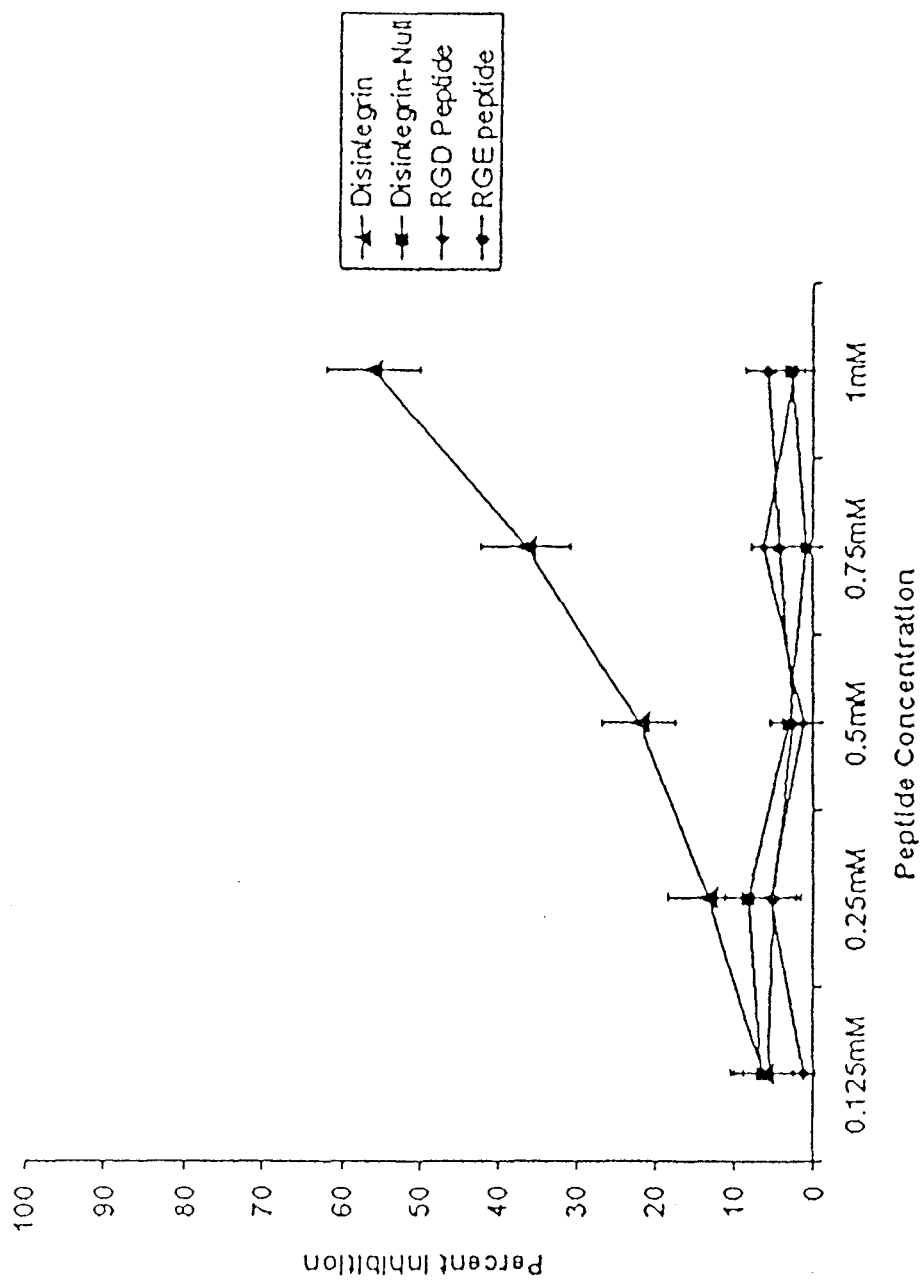
FIG. 2A is a graph showing that human cytomegalovirus (HMCV) gB disintegrin-like peptide inhibits CMV infection of normal human dermal fibroblast (NHDF) cells in a dose-dependent fashion.

Unless otherwise defined, all technical and scientific terms used herein have the same meaning as commonly understood by one of ordinary skill in the art of virology and/or pharmacology.

The present invention relates to methods and compositions for inhibiting the entry of viruses, specifically, herpesviruses into a host cell. Through antibody blocking and integrin knockout cell experiments, the present inventors have determined that integrins are utilized as CMV entry receptors to facilitate viral entry into a host cell. The inventors have also identified the presence of an integrin-binding gB disintegrin-like domain that is highly conserved among most herpesviruses. It has also been determined that the conserved viral gB disintegrin-like domains are capable of engaging cellular integrins. Thus the present invention reveals that the conserved viral gB disintegrin-like protein plays an important role in facilitating viral internalization into a host cell. The present invention therefore provides methods and compositions, such as anti-viral pharmaceutical compositions, for blocking the interaction between the gB disintegrin-like domain of a virus and the integrins of a putative host cell, thereby inhibiting and/or preventing entry of a virus into a host cell.

In one embodiment, the invention provides a method of inhibiting the entry of herpesviruses into a host cell by introducing, administering, or contacting an effective amount of an anti-viral agent, such as an isolated or synthetic peptide, with the cells of the subject in need of treatment for a viral infection. A herpesvirus infection is exemplary. The invention extends to the inhibition of viral entry of any virus in general, more particularly cytomegalovirus, and more particularly still herpesvirus. As used herein, the term "host cell" refers to an animal cell, including mammalian cells, and explicitly including human cells. The conserved gB disintegrin-like domain peptide of the invention may be mixed with a pharmaceutically acceptable, nontoxic carrier. Also, it is within the scope of the invention that the agent or peptide may be linked to another moiety, such as an internalizing peptide, an accessory peptide, or a transport moiety. The agent may be a peptidomimetic.

Peptides and peptidomimetics of the invention may be administered by any of a variety of routes depending upon the specific end use. These agents may be administered directly to virus-infected cells in general, and CMV-infected cells in particular. Direct delivery of such peptide therapeutics may be facilitated by formulation of the peptidyl compound in any pharmaceutically acceptable dosage form, e.g., for delivery orally, intratumorally, peritumorally, interlesionally, intravenously, intramuscularly, periolesionally, or topical routes, to exert local therapeutic effects. The preferred method of delivering the peptide into the cell is subcutaneously. Applicants envision that 50 to 350 mg of peptide is a suitable dose to be administered subcutaneously twice a day to a virus-infected subject.

The most suitable route in any given case will depend upon the use, particular type of agent containing the disintegrin-like domains, the subject involved, and the judgment of the medical practitioner. An agent of the invention may also be administered by means of controlled-release, depot implant or injectable formulations. The exact dose and regimen for administration of these agents will necessarily depend upon the needs of the individual subject being treated, the type of treatment, the degree of affliction or need and, of course, the judgment of the medical practitioner. In general, parenteral administration requires lower dosage than other methods of administration (e.g. topical), which are more dependent upon absorption.

In a preferred embodiment, the invention provides peptides having the conserved gB disintegrin-like domain of CMV including an amino acid consensus sequence represented by the following amino acid sequence: RX$_{5-8}$DLXXFX$_5$C (SEQ. ID. NOS: 1-4), where X can be any amino acid. Also, encompassed within the invention is the polypeptide RVCSMAQGTDLIRFERNIVC (SEQ. ID. NO: 5) or any conservative variant thereof having at least 80% amino acid sequence identity to SEQ. ID. NO: 5.

As used herein the term "amino acid" residue or sequence refers to abbreviations used herein for designating the amino acids based on recommendations of the IUPAC-IUB Commission on Biochemical Nomenclature (see *Biochemistry* (1972) 11:1726-1732). In certain embodiments, the amino acids used in the invention are those naturally occurring amino acids found in proteins, or the naturally occurring anabolic or catabolic products of such amino acids, which contain amino and carboxyl groups. This term further includes synthetic analogs, derivatives of any specific amino acid referred to herein (e.g., N-methyl derivatives, glycosylated derivatives, and the like), as well as C-terminal or N-terminal-protected amino acid derivatives (e.g., modified with an N-terminal or C-terminal protecting group such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid). Also included are the (D) and (L) stereoisomers of such amino acids when the structure of the amino acid admits of stereoisomeric forms. Other suitable amino acids will be recognized by those skilled in the art and are included in the scope of the present invention.

It must also be noted that CMVs are host-specific, and share very little identity over the entire glycoprotein B amino acid sequence. In contrast, however, a sequence alignment of the gB disintegrin-like domain portion of the present invention, taken across various mammalian species, shows a greater than 80% amino acid sequence identity. In fact, disintegrin-like domains in CMV from a variety of species, such as human, mouse, rhesus, baboon, guinea pig, and porcine strains, have been identified. (See FIG. 1B.) Other viruses closely related to the CMV, such as beta human herpesviruses-6A, 6B and 7 have also been identified to possess a gB disintegrin-like domain. Furthermore, the disintegrin-like domains have been identified in more distantly related gamma herpesviruses. These more distant viral families include, for example Epstein-Barr virus (EBV) which has a disintegrin-like sequence of RVCELSSHGDLFRFSSDIQC (SEQ. ID. NO: 6). The EBV disintegrin-like domain exhibits a 45% amino acid sequence identity to its corresponding HCMV domain. Likewise, Kaposi's sarcoma-associated herpesvirus (KSHV) has a disintegrin-like sequence of RVCSASITGELFRFNLEQTC (SEQ. ID. NO: 7). KSHV has a (D to E) substitution in its disintegrin-like consensus sequence. The KSHV disintegrin-like domain exhibits a 40% amino acid sequence identity to its corresponding HCMV domain. Thus, these conserved domains may also play a role in the entry of viruses beyond CMV.

It is believed that because many viruses, both close and distant in evolutionary terms to HCMV, possess disintegrin-like domains, it is foreseeable that these other viruses will behave similarly (i.e., by interfering with virus-integrin engagement) to block viral entry into a host cell. Therefore, it is envisioned that peptides directed to the sequence encompassing the disintegrin-like domain can be used as the active agent in a pharmaceutical composition to inhibit viral internalization into a host cell. While not being limited to any particular underlying mechanism or biological phenomenon, it is believed that the active ingredients of the present invention function by interfering with virus-integrin engagement, thereby blocking viral entry in a host cell.

Likewise, a peptidomimetic therapeutic drug, suitable for delivery to all parts of a mammal, suitably a human may be designed based on the consensus sequence of SEQ. ID. NOS: 1-4.

Because integrins have also been implicated in cellular migration, survival and angiogenesis, the peptides and peptidomimetics disclosed herein can also be used as an active agent in anti-cancer therapies.

In yet another embodiment, the invention provides antibodies (monoclonal or polyclonal) produced against disintegrin-like peptides. These antibodies exhibit therapeutic potential as anti-viral agents in general and anti-viral agents against CMV, herpesviruses, and the like. These antibodies are capable of binding the disintegrin-like domain and blocking the engagement of integrins, thereby inhibiting viral internalization into a host cell.

Indeed, as described below in the examples, a cell line lacking the β1 integrin is very poorly infected by HCMV. When β1 integrin was expressed and added back to the cells, the infection was restored. In addition, the examples demonstrate that antibodies to β1-containing integrins block HCMV entry. On this point, it is relevant to note that β1-containing integrins are expressed on all vertebrate cells. Furthermore, antibodies to the β3 subunit also block viral entry (but to a lesser extent). Similarly, antibodies directed against the alpha subunits showed blockage of viral entry with antibodies to α2, αV, and α6.

To produce specific antibodies against the conserved gB disintegrin-like domain, the peptide containing an amino acid consensus sequence represented by the formula: $RX_{5-8}DLXXFX_5C$, as set forth in SEQ. ID. NOS: 1-4, where X can be any amino acid is injected into an animal host capable of generating an immune response to the peptide. Also in accordance with the invention, the antibody raised against the polypeptide can have the sequence RVCSMAQGTDLIRFERNIVC, as set forth in SEQ. ID. NO: 5 or 80% amino acid sequence identity to SEQ. ID. NO: 5.

Methods for injecting an immunogenic peptide into an animal host are well known, and disclosed in greater detail hereinbelow. One having ordinary skill in the art is capable of selecting a host in which an immune response may be induced. A typical system involves injecting the selected peptide into mice, rabbits, or guinea pigs to produce an IgG response. Serum obtained from such immunized animals contains polyclonal antibodies having specificity against the immunogen. Alternatively, the selected peptide can be injected into suitably primed mice to induce antibody-producing B-cells which can be fused with an immortalized cell line using conventional techniques, to prepare hybridomas that secrete monoclonal antibodies diagnostic for one strain of herpesvirus or monoclonal antibodies that recognize more than one herpesvirus strain.

The specificity of the polyclonal or monoclonal antibodies can be assessed by screening the antibodies in an immunofluorescence assay using cells known to be infected with herpesvirus. In particular, the antibodies obtained can be incubated with herpesvirus-infected cells. The antibodies can also be used in an immunoassay of cellular extracts or lysates, where, after infection, the cell membranes of the host cells are weakened or removed and the immediate early protein is assayed after release from the cells.

In addition to the actual gB disintegrin-like domain, the sequences flanking the domain may be important to the specificity and effectiveness of the peptide, peptidomimetic or antibody used to inhibit viral internalization into the host cell. Thus, a peptide encompassing the gB disintegrin-like domain of EBV and the flanking sequences surrounding the domain (see, for example, FIG. 5) is expected to be more specific and effective in blocking EBV entry into a host. Thus, it is believed that amino acids surrounding the consensus sequence may be equally important as the actual consensus sequence in targeting the virus to specific integrin heterodimers (α2β1, α6β1 and αVβ3), while preventing engagement with others.

Polypeptide Synthesis:

Polypeptides according to the present invention can be fabricated synthetically using any means now known in the art or developed in the future. Solid-phase peptide synthesis is generally preferred. Very briefly, in solid-phase synthesis, the desired C-terminal amino acid residue is linked to a polystyrene support as a benzyl ester. The amino group of each subsequent amino acid to be added to the N-terminus of the growing peptide chain is protected with tert-butoxycarbonyl, (Boc), 9-fluorenylmethoxycarbonyl (Fmoc), or another suitable protecting group. Likewise, the carboxylic acid group of each subsequent amino acid to be added to the chain is activated with N,N-dicyclohexylcarbodiimide (DCC) and reacted so that the N-terminus of the growing chain always bears a removable protecting group. The process is repeated (with much rinsing of the beads between each step) until the desired polypeptide is completed. In the conventional route, the N-terminus of the growing chain is protected with a Boc group, which is removed using trifluoracetic acid, leaving behind a protonated amino group. Triethylamine is used to remove the proton from the N-terminus of the chain, leaving a free amino group, which is then reacted with the activated carboxylic acid group from a new protected amino acid. When the desired chain length is reached, a strong acid, such as hydrogen bromide in trifluoracetic acid, is used both to cleave the C-terminus from the polystyrene support and to remove the N-terminus protecting group. The entire process has been automated and robotic polypeptide synthesizers are available from a number of commercial suppliers, e.g., Applied Biosystems, Foster City, Calif. Peptide synthesis is widely employed and well known. For a full treatment, see, for example, Bodanszky, M.; Bodanszky, A. *The Practice of Peptide Synthesis, 2nd Edition;* Springer Verlag: Berlin, 1995.

Antibody Production:

Monoclonal and polyclonal antibodies to the gB disintegrin-like peptides disclosed herein can be fabricated by any means now known in the art or developed in the future. A number of different protocols are conventional and well-known in the art.

Briefly, to prepare monoclonal antibodies, the peptide antigen (a gB disintegrin-like peptide) is prepared for injection either by emulsifying it into a suitable adjuvant (e.g., Freund's) or by homogenizing a polyacrylamide gel slice that contains the protein antigen. The test animals, normally mice, are immunized at 2- to 3-week intervals. Test bleeds are collected seven days after each booster immunization to monitor serum antibody levels. Test animals are chosen for hybridoma fusions when a sufficient antibody titer is reached.

Spleen cells from the immunized animals are then fused with myeloma cells to yield antibody-producing hybridoma cells. Briefly, freshly-harvested spleen cells from the immunized animals and myeloma cells are co-pelleted by centrifugation and then fused by adding polyethylene glycol (PEG) to the pellet. The cells are then centrifuged again and the PEG solution is diluted by adding fresh medium. The fused cells are then centrifuged, resuspended in a selection medium, and aliquotted into a 96-well plate. The hybridomas are then grown to 10-50% confluence and assayed for the production of antigen-specific antibody.

The hybridoma cell lines are then cloned by limiting dilution. Briefly, the hybridomas to be cloned are diluted to roughly 0.8 cells per well. This dilution factor yields 36% of the wells having one cell per well (according to Poisson statistics). When the cultures are 10-50% confluent, antibody production is assayed by enzyme-linked immunosorbent assay (ELISA). Two or more cloning procedures are carried out until >90% of the wells containing single clones are positive for antibody production. The best of the cell lines can be stored by suspending the cells in dimethyl sulfoxide/fetal calf serum and then freezing them rapidly in a dry ice-ethanol and glycerol bath, followed by transfer to liquid nitrogen storage. The cells can be re-activated by thawing rapidly at 37° C., with immediate replacement of the freezing medium with culture medium.

High-titer monoclonal antibody preparations can be obtained directly from the hybridoma supernatants or from the ascites fluid of mice inoculated intraperitoneally with monoclonal antibody-producing hybridoma cells. For producing antibody supernatants, the hybridoma is grown and split 1 to 10. The cells are then overgrown until cell death occurs. The supernatant is then harvested and the antibody titer is determined. The supernatant can be used as is or the antibody can be purified from the supernatant. To produce ascites fluid, test animals inoculated intraperitoneally with monoclonal antibody-producing hybridoma cells. The ascites fluid is collected several times after injection of the cells. The ascites fluid is heat-inactivated and the antibody titer is determined by ELISA.

Monoclonal and polyclonal antibody production is widely employed and well known. For a full treatment, see, for example, *Current Protocols in Molecular Biology*, volume 2, chapter 11 (copyright 1994-1998, John Wiley & Sons).

Pharmaceutical Methods and Compositions:

Another aspect of the invention provides pharmaceutical compositions, for medical use, comprising an active compound, i.e., a gB disintegrin-like polypeptide, or a pharmaceutically-acceptable salt or analog thereof, or an antibody as disclosed herein, optionally in combination with an acceptable carrier and optionally in combination with other therapeutically-active ingredients or inactive accessory ingredients. The carrier must be pharmaceutically-acceptable in the sense of being compatible with the other ingredients of the formulation and not deleterious to the recipient. The pharmaceutical compositions include those suitable for oral, topical, inhalation, rectal or parenteral (including subcutaneous, intramuscular and intravenous) administration.

The formulations may conveniently be presented in unit dosage form and may be prepared by any of the methods well known in the pharmaceutical arts. The term "unit dosage" or "unit dose" is denoted to mean a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active agent into association with a liquid or solid carrier and then, if necessary, shaping the product into the desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface-active or dispersing agents. Molded tablets may be made by molding in a suitable machine a mixture of the powdered active compound with any suitable carrier.

Formulations suitable for parenteral administration conveniently comprise a sterile preparation of the active compound in, for example, water for injection, saline, a polyethylene glycol solution, and the like, which is preferably isotonic with the blood of the recipient.

Useful formulations also comprise concentrated solutions or solids containing the active agent which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefor such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 5.0% by weight.

Compositions suitable for rectal administration, comprise a suppository, preferably bullet-shaped, containing the active ingredient and pharmaceutically-acceptable vehicles therefor such as hard fat, hydrogenated cocoglyceride, polyethylene glycol and the like. In suppository formulations, the subject compounds are preferably utilized at concentrations of from about 0.1% to 10% by weight.

Compositions suitable for rectal administration may also comprise a rectal enema unit containing the active ingredient and pharmaceutically-acceptable vehicles therefor such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the subject compounds are preferably utilized at concentrations of from about 5.0-10% by weight.

Useful formulations also comprise concentrated solutions or solids containing the active ingredient which upon dilution with an appropriate solvent, preferably saline, give a solution suitable for rectal or vaginal administration. These compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of the active agent are preferably utilized at concentrations of from about 0.1% to 5.0% by weight applied to a dressing.

Compositions suitable for administration by inhalation include formulations wherein the active ingredient is a solid or liquid admixed in a micronized powder having a particle size in the range of about 5 microns or less to about 500 microns or liquid formulations in a suitable diluent. These formulations are designed for rapid inhalation through the oral passage from conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, e.g., diluents, buffers, flavoring agents, colorants, binders, surface-active agents, thickeners, lubricants, suspending agents, preservatives (including antioxidants) and the like.

As noted above, the amount of the active agent required to be effective for any indicated condition will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. In general, a suitable effective dose is in the range of about 0.1 to about 500 mg/kg body weight per day, preferably in the range of about 5 to about 350 mg/kg per day, calculated as the non-salt form of Formula I. The total daily dose may be given as a single dose, multiple doses, e.g., two to six times per day, or by intravenous infusion for a selected duration. For example, for a 75 kg human patient, a typical dose would be approximately 7.5 to 350 mg of peptide, administered subcutaneously twice a day. Dosages above or below the range cited above are within the scope of the present invention and may be administered to the individual patient if desired and necessary.

In general, the pharmaceutical compositions of this invention contain from about 0.5 mg to about 1.5 g active ingredient per unit dose and, preferably, from about 7.5 to about 500 mg per unit dose. If discrete multiple doses are indicated, treatment might typically be 100 mg of a peptide as disclosed herein given from two to four times per day.

The compounds according to the present invention may be administered prophylactically, chronically, or acutely. For example, such compounds may be administered prophylactically to inhibit the formation of cancers in the subject being treated, or to prevent viral infection in the subject being treated. In addition to the prevention of viral infection, chronic administration of the subject compounds will typically be indicated in treating recurring outbreaks of CMV and herpesvirus-mediated ailments. Acute administration of the subject compounds is indicated to treat, for example, aggressive flare-up of viral-mediated symptoms.

EXAMPLES

The following Examples are included solely to provide a more complete understanding of the present invention. The Examples do not limit the scope of the invention disclosed and claimed herein in any fashion.

Methods and Materials:

Sequence Alignment and Motif Search:

HCMV glycoproteins B, H, L, O, M, N and clinical isolates were analyzed for the following integrin recognition motifs: LDV, DGE, RGD, NGR, RRETAWA (SEQ. ID. NO: 10), REDV (SEQ. ID. NO: 11), SDGR (SEQ. ID. NO: 12), YIGSR (SEQ. ID. NO: 13), YIGSE (SEQ. ID. NO: 14), RGES (SEQ. ID. NO: 15), RSGIY (SEQ. ID. NO: 16), RSGD (SEQ. ID. NO: 17), DRDE (SEQ. ID. NO: 18), and SRYD (SEQ. ID. NO: 19) using DNAstar software (DNASTAR, Inc., Madison, Wis.). The results are shown in FIGS. 1A and 1B.

Cell Lines and Viruses:

Beta 1 integrin knockout fibroblasts (GD25) and Beta 1 integrin restored GD25 cells (GD25β1) were obtained (and are available) through the University of Wisconsin—Madison, Madison, Wis. Normal Human Dermal Fibroblasts (NHDFs), Mouse NIH 3T3 cells, and GD25 cells were cultured in Dulbecco's modified Eagle medium (DMEM) supplemented with 10% fetal calf serum (GIBCO—Carlsbad, Calif.) and antibiotics, in a 5% $CO_2$ atmosphere, at 37° C. GD25β1 cells were cultured as the other lines, but also contained 10 μg/mL puromyocin (Sigma—St. Louis, Mo.). Herpes simplex virus type I strain HSV-1(KOS)gL86, marked with the E. coli LacZ gene, was propagated in 79VB4 cells. Murine cytomegalovirus (MCMV) (Smith strain; ATCC VR-194) was prepared and titered on NIH 3T3 cells as previously described.[43] MCMV-GFP (strain RVG102), marked with enhanced green fluorescent protein (GFP) under the control of the immediate early 1/3 promoter, was constructed as described in the literature.[43] (MCMV-GFP is also available from Eastern Virginia Medical College, Norfolk, Va.). HCMV AD169 was grown and titered on NHDFs as previously described. HCMV with immediate early protein 2-GFP was a generous gift from D. Spector (UC—San Diego).[46] Kaposi's sarcoma-associated herpesvirus (KSHV) was grown in BCBL1 cells as previously described.[41] HCMV, KSHV and VSV were incubated with 1% diI (a dialkylcarbocyanine dye available from Molecular Probes, Eugene, Oreg.) for 30 minutes at room temperature. Virions were then gradient purified to remove free dye as previously described.[6,41,47]

Production and Purification of $gB_{DLD}$:

DNA sequence corresponding to amino acids 57-146 of HCMV AD 169 glycoprotein B disintegrin-like domain ("$gB_{DLD}$") was cloned into the bacterial expression vector pET-28a containing an N-terminal His-Tag with thrombin cleavage site and kanamycin resistance. (Commercially available from Novagen, San Diego, Calif.) $gB_{DLD}$ production was induced by the addition of 1 mM isopropyl-βD-thiogalactopyranoside (IPTG). E. coli Tuner strain containing pET-28a:$gB_{DLD}$ was grown at 37° C. in Luria-Bertani medium containing kanamycin (50 μg/mL) to an optical density at 600 nm of approximately 0.6. IPTG (1 mM) was added and the plates were incubated continuously for 4 h at 37° C. Cells were harvested by centrifugation at 4000 r/min for 10 min and pellets were resuspended in 1% Triton X-100/Ni-NTA buffer (300 mM NaCl/50 mM Tris-HCL pH 7.9) and lysed by 3×60 s bursts of sonication. The lysate was centrifuged at 15,000 r/min for 15 minutes at 4° C. The 8M urea/Ni-NTA fraction was then poured into a chromatography column containing nickel-nitriloacetic acid agarose (Ni-NTA) beads at 4° C. and allowed to flow through. The column was then washed three times with ice cold 8M urea/NiNTA buffer. The protein was eluted from the column with 300 mM imidazole/8M urea/Ni-NTA buffer. Eluate from the column was placed onto a S-200 sizing column and fractions were collected at regular intervals. Fractions containing protein were determined by measuring the absorbance of each fraction at 214 nm. Fractions that corresponded to absorption peaks were analyzed by sodium dodecyl sulfate polyacrylamide electrophoresis (SDS-PAGE) to determine the size of the protein. The absorption peak fractions that contained a protein of the same size as the $gB_{DLD}$ were pooled and concentrated using a Ni-NTA column. The concentrated fractions were dialyzed extensively against 55 mM 2-(N-morpholino) ethanesulfonic acid (MES), pH 5.5, 300 mM NaCl to remove urea and glycerol. Solubility in this buffer is approximately 1 mg/mL. Any precipitate was removed by centrifugation at 13,000 r/min for 30 min at 4° C. Starting with a 1 L culture of E. coli, this procedure yielded approximately 1 mg of $gB_{DLD}$ at 1 mg/mL.

Antibodies, Peptides and Soluble Proteins:

Neutralizing Beta 1 integrin antibody DE9 (IgG),[22,23] was obtained (and is available) from the Childrens Hospital of Philadelphia, Philadelphia Pa.). All other integrin antibodies [α1 (FB12), α2 (PIE6), α3 (PIβ5), α4 (PIH4), α5 (PID6), αV (M9), α6 (GoH$_3$), β3 (25E11) αVβ3 (LM609)] were purchased from Chemicon, Inc. (Temecula, Calif.). Monoclonal antibody 1203, which recognizes the immediate early (IE) gene products of HCMV, also referred to herein as mouse anti-IE monoclonal antibody, was purchased from the Rumbaugh-Goodwin Institute for Cancer Research, Inc. (Plantation, Fla.). Monoclonal antibody 27-78, which recognizes antigenic domain 1 (AD-1) of gB, was obtained (and is available) from the University of Alabama—Birmingham, Ala.).[44] A monoclonal antibody raised against the major tegument protein, pp65, was purchased from Advanced Biotechnologies, Inc. (Columbia, Md.). Rabbit polyclonal anti-MCMV e1,[45] which recognizes the MCMV early protein was obtained (and is available) from Eastern Virginia Medical College. Fluorescein-conjugated goat anti-mouse secondary antibody, fluorescein-conjugated goat anti-rabbit secondary antibody, and horseradish peroxidase (HRP)-conjugated goat anti-mouse secondary antibody were purchased from Pierce (Rockford, Ill.). HCMV gB disintegrin-like peptide (RVCS-MAQGTDLIRFERNIIC, SEQ. ID. NO: 8) and HCMV gB disintegrin-like Null peptide (AVCSMAGGTAAIRAER-NIIC, SEQ. ID. NO: 9) were synthesized, purified by reverse-phase HPLC, and the sequence confirmed by mass spectrometry. These two peptides were custom synthesized by, and purchased from, the University of Wisconsin Biotechnology Center Peptide Synthesis Facility (University of Wisconsin—Madison). RGD and RGE peptides were purchased from Sigma (St. Louis, 388 Mo.).

Protein Binding Assay:

Normal human dermal fibroblasts were chilled to 4° C., washed three times with cold MES buffer and blocked with 1 mg/mL bovine serum albumin (BSA) for 30 minutes at 4° C. Unbound BSA was removed with cold MES washes (×4). The indicated amounts of $gB_{DLD}$ were added to each well for 90 minutes at 4° C. Cells were then washed three times with cold MES, twice with cold (phosphate-buffered saline (PBS) and fixed with 3% paraformaldehyde. An ELISA was then performed probing with anti-His rabbit polyclonal antibody (Santa Cruz Biotechnology, Santa Cruz, Calif.) and anti-rabbit HRP (Pierce). Absorbance was measured at 405 nm.

Virus Entry Assay:

For CMV entry assays, subconfluent cells were grown on glass coverslips in 12-well plates. Integrin neutralizing antibodies or peptides were incubated in serum-free DMEM with cell monolayer for 30 minutes at 37° C. Cells were washed with phosphate-buffered saline (PBS) and incubated with HCMV strain AD169, MCMV Smith strain, or MCMV-GFP for 60 minutes at 37° C. Any non-penetrated virus was inactivated with low-pH citrate buffer (40 mM citric acid, 10 mM KCl, 135 mM NaCl, pH 3.0). The cells were incubated 20-24 hours at 37° C. in DMEM supplemented with 2% bovine calf serum (BCS). Immunofluorescence analysis was performed as previously described[28] with either mouse anti-IE monoclonal antibody 1203, mouse anti-pp65 monoclonal antibody or rabbit anti-MCMV e1 polyclonal, followed by detection with a fluorescein-conjugated goat anti-mouse secondary or a fluorescein-conjugated goat anti-rabbit secondary antibody. Nuclei were stained with 300 nM 4',6-diamidino-2-phenylindole (DAPI). Experiments were performed in triplicate with a minimum of 1000 cells scored per coverslip. For the HSV entry assay, peptide was incubated with NHDF cells for 30 minutes, challenged with HSV-1(KOS)gL86, and any non-penetrated virus was inactivated with low-pH citrate buffer. Cells were incubated 6 hours at 37° C. in DMEM supplemented with 10% BCS prior to lysis (100 mM sodium phosphate, 10 mM KCl, 1 mM magnesium sulfate, 0.1% NP-40, pH 7.4). β-galactosidase activity was measured by addition of o-nitrophenyl-β-D-galactopyranoside (ONPG) and the absorbance was monitored at 420 nm.

Virus Binding Assay:

NHDF cells were grown in 96-well plates and treated with integrin-neutralizing antibodies, peptides, or heparin for 60 minutes at 4° C. Cells were then challenged with HCMV AD 169 at a multiplicity of infection (MOI) of 5 pfu/cell for 60 minutes at 4° C. Unbound virus was removed and cells were washed and fixed with 3% paraformaldehyde. Bound HCMV was detected with monoclonal antibody 27-78, horseradish peroxidase (HRP)-conjugated goat anti-mouse secondary antibody, and ImmunoPure TMB Substrate Kit (Pierce, Rockford, Ill.). Absorbance was measured at 450 nm. All experiments were performed in triplicate.

Cell-Cell Spread Assay:

GD25 or GD25β1 cells were grown to complete confluence in 6-well plates. One hundred (100) pfu of MCMV-GFP was added to cells in serum-free DMEM and adsorbed for 20 minutes at 37° C. Inoculants were aspirated off, washed and replaced with DMEM containing 2% BCS for 9 days.

HCMV Infectivity Assay:

NHDFs were washed three times with MES buffer followed by the addition of $gB_{DLD}$ for 60 minutes at 37° C. Cells were then washed twice with MES buffer, three times with PBS and inoculated with HCMV-GFP (MOI=0.5) in serum-free DMEM. After 60 minutes, virus was removed and a 30 second, low-pH citrate wash was performed to remove extracellular virus. Twenty-four hour, post-infection cells were harvested and flow cytometry was performed to assay for GFP-positive cells.

HCMV Fusion Assay:

NHDFs were washed three times with MES buffer followed by the addition of $gB_{DLD}$ for 60 minutes at 37° C. Cells were then washed twice with MES buffer, three times with PBS and inoculated with diI-labeled HCMV-GFP (MOI=0.5), KSHV or VSV in serum-free DMEM. After 60 minutes, virus was removed and a 30-second, low pH citrate wash was performed to remove extracellular virus. Flow cytometry was performed 3 hrs post-infection to assay for fused (red) cells. Alternatively, microscopy was performed 24 hrs post-infection to assess GFP expression (immediate early gene expression), diI staining (fusion) and phase (cytopathic effect).

Integrin Co-Immunoprecipitation Assay:

A T-175 flask of NHDFs was grown to complete confluence, washed three times in MES buffer and lysed in 1 mL MES buffer+1% TX-100 (a detergent). Lysate was spun at 10,000 g for 10 minutes to remove cell debris. Cell lysate (350 μL) was then incubated with 20 μg gB$_{DLD}$ for 4 hours at 4° C. The lysate+gB$_{DLD}$ mixture was then incubated with 50 μL Ni beads overnight at 4° C. Nickel beads were then washed three times and protein eluted by boiling and then adding reducing SDS-PAGE buffer. Proteins were separated by SDS-PAGE and Western blotted for β1 integrin (Chemicon-1965) or β3 (Chemicon) as previously described.[48]

Results:

The gB Disintegrin-Like Domain is Highly Conserved throughout Herpesviridae:

Integrin expression patterns on HCMV-susceptible cells, HCMV-induced cellular morphological changes, and overlapping signaling capabilities suggest integrins may be involved in HCMV entry. Because all viruses known to utilize integrins as entry receptors have been shown to do so by extracellular matrix (ECM) protein mimicry, all HCMV structural glycoproteins were inspected (via computer matching analysis) for the integrin-binding sequences LDV, DGE, RGD, NGR, RRETAWA (SEQ. ID. NO: 10), REDV (SEQ. ID. NO: 11), SDGR (SEQ. ID. NO: 12), YIGSR (SEQ. ID. NO: 13), YIGSE (SEQ. ID. NO: 14), RGES (SEQ. ID. NO: 15), RSGIY (SEQ. ID. NO: 16), RSGD (SEQ. ID. NO: 17), DRDE (SEQ. ID. NO: 18), and SRYD (SEQ. ID. NO: 19). It was found that all HCMV glycoproteins lack ECM-derived integrin binding sequences, but the gB protein does contain the integrin binding disintegrin-like consensus sequence RX$_{(6-8)}$DLXXF (SEQ. ID. NOS: 20, 21, and 22) found in the ADAM family of proteins.[15]

The gB sequences of forty-four HCMV clinical isolates and two laboratory strains AD169 and Towne were analyzed for the presence of the disintegrin-like domain. The results are presented in FIG. 1A. The 20 amino acids encompassing the gB disintegrin-like domain shared a 98% identity, with greater than 99% conservation of the disintegrin-like consensus in a positional-dependent manner. In FIG. 1A, conserved sequences are shown in bold; the conserved residues of the gB disintegrin-like domain are shown in bold underline. Non-conserved residues are shown in italics. For each isolate the PubMed/Genbank accession number and protein identification code is given.

FIG. 1B shows that among other beta herpesviruses, the 20 amino acids encompassing the gB disintegrin-like domain share an 86.5% identity with perfect conservation of the disintegrin-like consensus except for a conservative L→F substitution in Baboon CMV gB. (Overall conserved sequences shown in bold, the conserved gB disintegrin-like residues shown in bold underline, non-conserved sequences shown in italics.) Furthermore, as is also shown in FIG. 1B, the gB disintegrin-like domain is present in many gamma herpesviruses, but absent in alpha herpesviruses, such as herpes simplex virus (HSV).

The import of these results is that the disintegrin-like domain is found in a region of gB implicated in receptor binding and virus-cell fusion.[19,20] These findings thus represent the first reported case of disintegrin-like domain mimicry by a virus.

CMV Utilizes Integrins in a Disintegrin-Like, Domain-Dependent Manner:

To test the role of the gB disintegrin-like domain in cytomegalovirus entry, peptides corresponding to the 20 amino acids encompassing this domain were synthesized. Additionally, gB disintegrin-like null peptides containing alanine substitutions in the disintegrin-like consensus residues were also synthesized. Both were analyzed for their effects on HCMV entry. HCMV infectivity of fibroblasts was also tested after treatment with RGD and RGE peptides to rule out the possibility of RGD structural mimicry in these glycoproteins.[21]

FIG. 2A presents the results of a series of assays wherein NHDFs were treated with HCMV gB disintegrin-like peptide, gB disintegrin-like Null peptide, RGD, or RGE peptide prior to HCMV challenge (as indicated in the FIG. 2A). Infectivity was determined by IE gene expression. The y-axis shows percent inhibition of viral infectivity compared to infectivity seen with no treatment. FIG. 2A shows that HCMV was able to infect RGD-, RGE-, and gB disintegrin-like null peptide-treated cells; however, a dose-dependent inhibitory response to infection was observed when the fibroblasts were treated with gB disintegrin-like peptide. FIG. 2A clearly shows that treating the cells with the gB disintegrin-like peptide inhibited HCMV infection. Given the high degree of conservation of the gB disintegrin-like domain throughout the beta herpesvirus subfamily (FIG. 1A), the effect of the human gB disintegrin-like peptide on mouse cytomegalovirus (MCMV) infectivity was then tested.

Figure 2B:
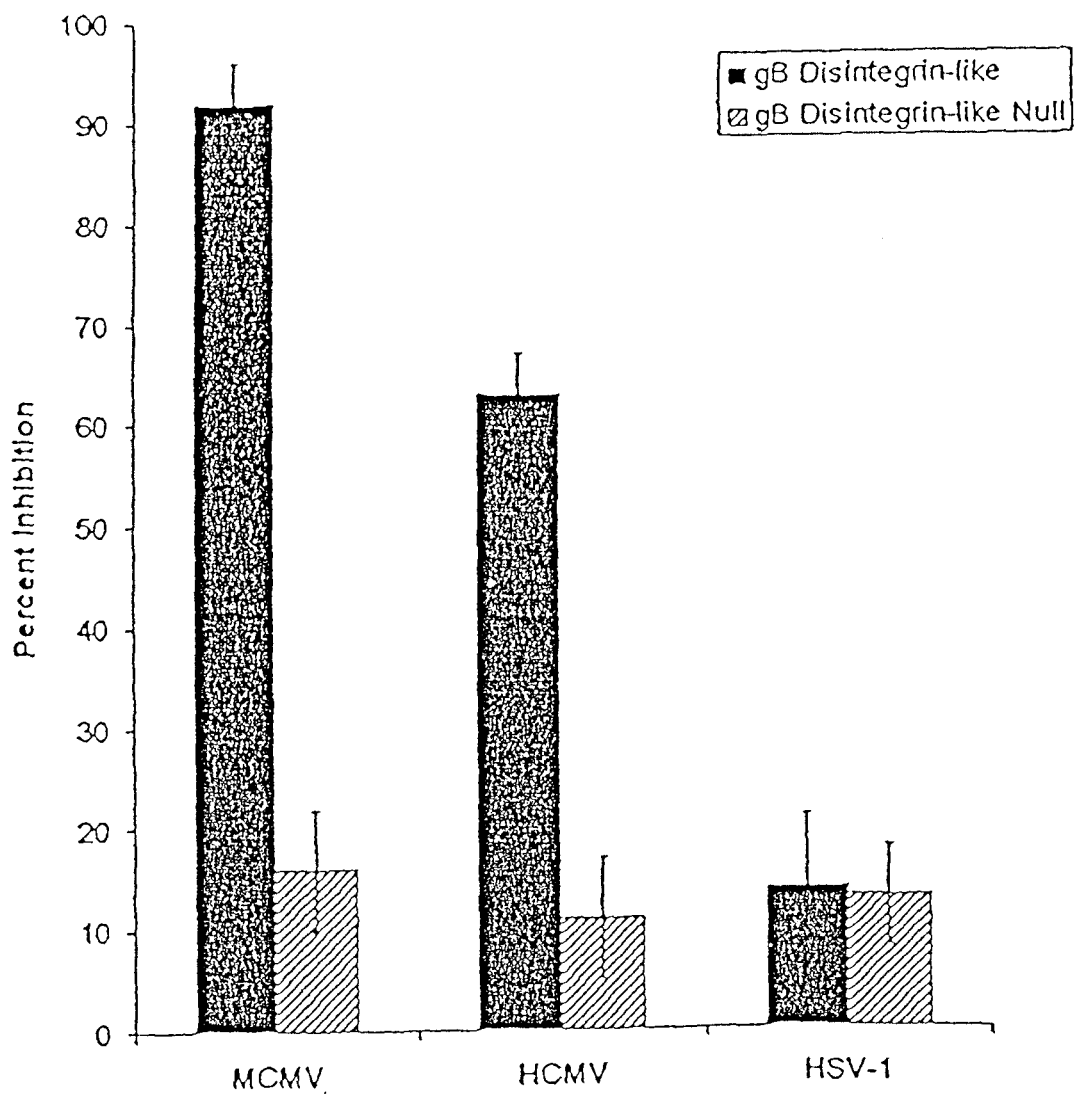
FIG. 2B is a histogram depicting the inhibition of murine cytomegaloviruse (MCMV), HCMV or herpes simplex virus-1 (HSV-1) infection of murine 3T3 cells and NHDF cells treated with HCMV gB disintegrin-like peptide or HCMV gB disintegrin-like null peptide.

FIG. 2B presents the results of a series of assays wherein murine 3T3 or NHDF cells were treated with HCMV gB disintegrin-like peptide or HCMV gB disintegrin-like null peptide, and then challenged with MCMV, HCMV or herpes simplex virus-1 (HSV-1). From the percent inhibition of viral entry shown on the y-axis of FIG. 2B, it is clearly shown that treatment of mouse fibroblasts with the gB disintegrin-like peptide resulted in a dramatic reduction in MCMV infectivity. By contrast, the gB disintegrin-like peptide had no effect on the ability of a virus that lacks the gB disintegrin-like domain, herpes simplex virus-1 (HSV-1), to infect cells.

Integrin-Blocking Antibodies Inhibit HCMV Infection:

Given the inhibitory effects of the gB disintegrin-like peptides as shown in FIGS. 2A and 2B, the role of specific cellular integrins in HCMV entry was tested. A variety of antibodies designed to bind the natural ligand-binding pocket of β1 integrin and β3 integrin subunits were tested. β1 integrin and β3 integrin are the two most broadly distributed integrins. The results are presented in FIGS. 3A, 3B, and 3C. The β1 integrin neutralizing antibody DE9 is known in the art.[22-25]

Figure 3A:
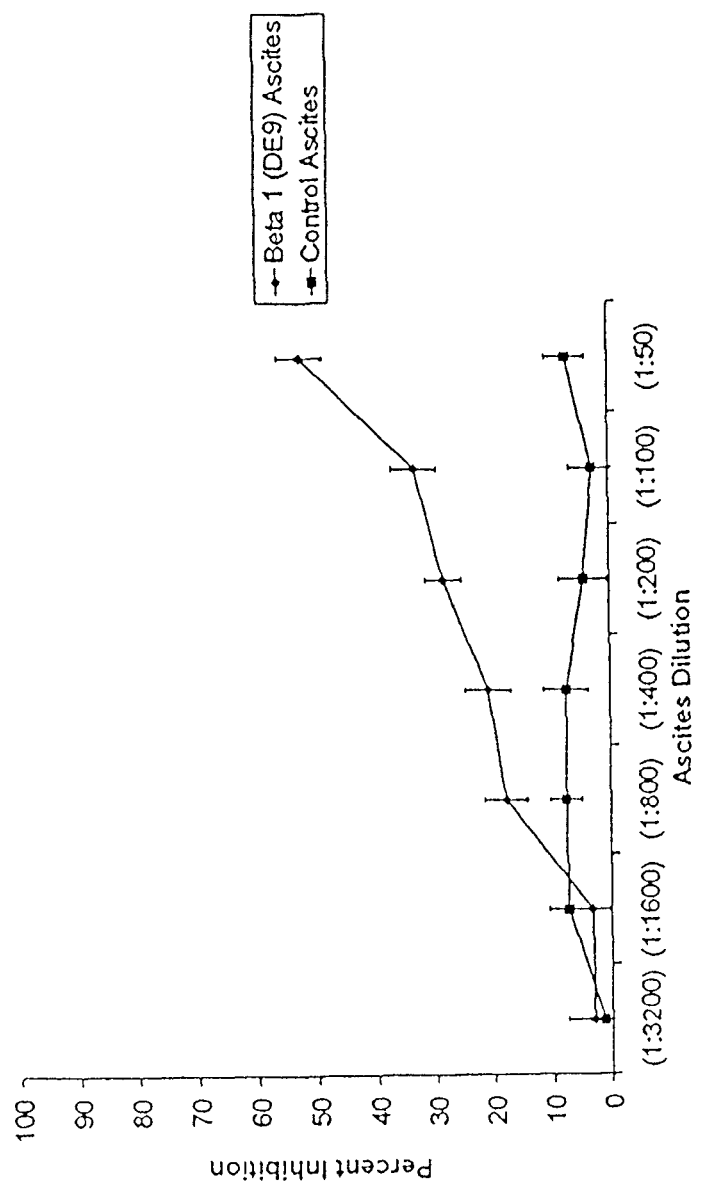
FIG. 3A is a graph showing that integrin-neutralizing antibodies inhibit HCMV infectivity in a dose-dependent fashion. The graph depicts the results of treating NHDFs with DE9 antibody.
Figure 3C:
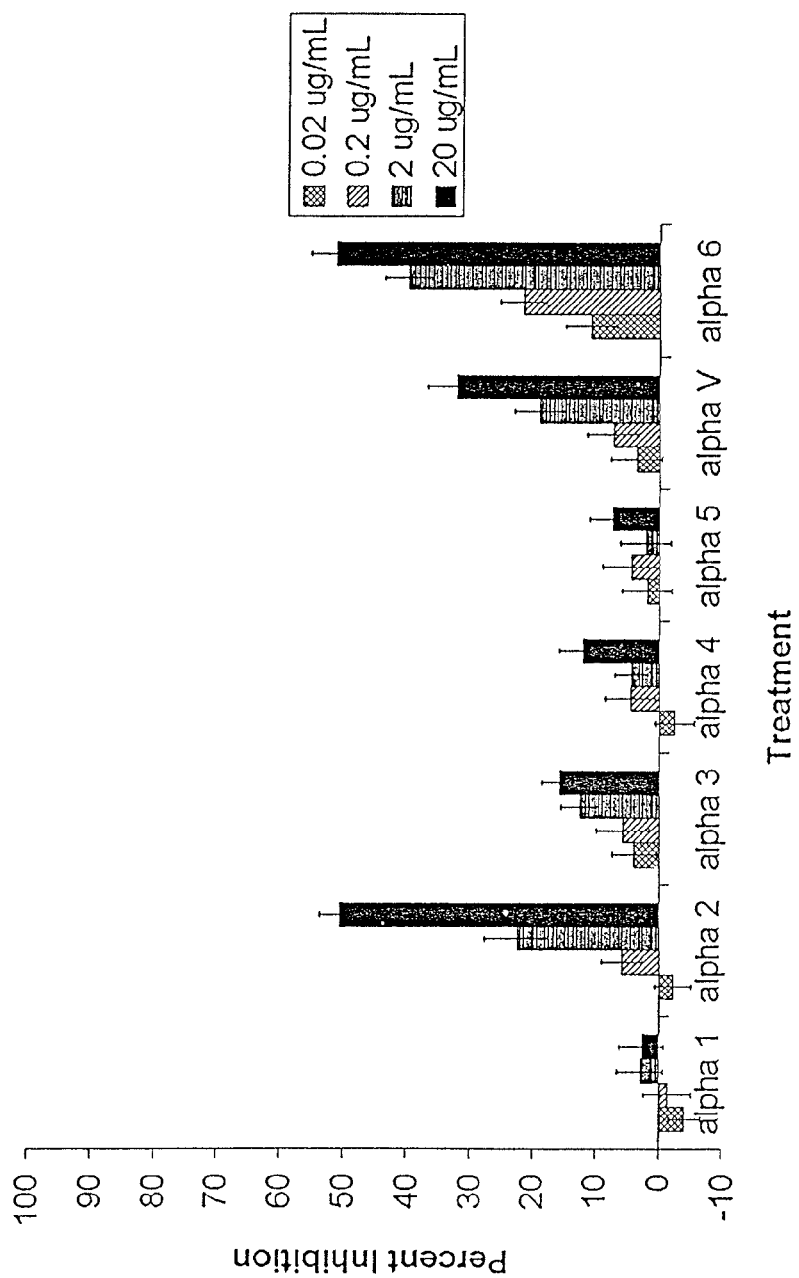
FIG. 3C is a histogram showing the results of treating NHDFs with a panel of alpha-integrin subunit neutralizing antibodies. Treating NHDFs with monoclonal antibodies to the α2 and β6 integrin subunits inhibited HCMV infection similarly, while monoclonal antibodies to the αV integrin subunit had a moderate inhibitory activity. Neutralizing antibodies to other abundantly expressed integrins such as α5, or moderately expressed integrins (α1, α3) and integrins expressed at low levels (α4) inhibited HCMV entry to a much lesser extent.

FIGS. 3A, 3B, and 3C collectively demonstrate that integrin-neutralizing antibodies inhibit HCMV infectivity. Specifically, FIG. 3A shows that treating NHDFs with DE9 antibody inhibited HCMV infection in a dose-dependent manner, while treating the cells with control ascites had no effect on viral infectivity. The percent inhibition of infection as compared to infectivity seen with no treatment is shown on the y-axis of FIG. 3A. From the percent inhibition of viral entry shown on the y-axis, it can be clearly seen that integrin-neutralizing antibodies are capable of inhibiting HCMV infection. In addition, neutralizing monoclonal antibodies to the β3 integrin subunit also inhibited infection, in contrast to both the isotype control or β1 integrin subunit non-neutralizing antibodies, which showed no inhibitory activity. See FIG. 3B. These data are consistent with inhibition levels seen by other integrin-utilizing viruses and implicate a role for both β1 and β3 integrin subunits in HCMV entry.

A panel of alpha integrin subunit-neutralizing antibodies was used to identify specific cellular integrin heterodimers involved in viral infection. Treating human fibroblasts with monoclonal antibodies to either of the α2 or β6 integrin subunits inhibited HCMV infection. Monoclonal antibodies to the αV integrin subunit had only a moderate inhibitory activity. See FIG. 3C. Neutralizing antibodies to other abundantly expressed integrins such as α5, or moderately expressed integrins (α1, α3) and integrins expressed at low levels (α4) did not inhibit HCMV entry (FIG. 3C). Combined, these data provide clear evidence that a specific subset of integrin heterodimers (α2β1, α6β1 and αVβ3) function as HCMV entry receptors.

Cells Lacking β1 Integrin Exhibit Decreased CMV Infectivity:

To confirm a role for β1 integrins in CMV infection, virus entry assays were performed using fibroblasts isolated from β1 integrin knockout mice (GD25),[26] or in GD25 cells with restored β1 integrin expression (GD25β1). The results are shown in FIGS. 4A and 4B.

FIG. 4A is a histogram showing the results of an assay wherein GD25, GD25βI and NHDF cells were first treated with β1, β3, or β1+β3 antibodies, followed by HCMV infection. The percent viral infectivity as compared to infectivity seen with no treatment is shown on the y-axis. Because the GD25 cells do not express the βI integrin subunit, they are unable to transport any α-subunit that exclusively partners with β1-subunits (α1, α2, α3, α5 α7, α8, α9, α10, α11) to the cell surface. Normalized to β1 integrin restored cells (GD25β1), GD25 fibroblasts allowed for only 39%±3.4 infectivity of HCMV. Consistent with data presented above, β1 integrin-neutralizing antibody reduced HCMV infectivity in GD25β1 and NHDF cells to comparable levels seen in GD25 untreated samples. β3-neutralizing antibody treatment also reduced HCMV infectivity in GD25β1 and NHDF cells to approximately 60% of levels seen in each respective cell line without antibody treatment. The same treatment further reduced infectivity in GD25 cells to 28%±3.2. Co-treatment with both βI and β3 antibodies reduced HCMV infectivity to approximately 25% in all cell lines tested, a greater reduction in infectivity seen with either individual antibody treatment.

FIG. 4B is a histogram showing the results of an assay wherein GD25, GD25β1 and 3T3 cells were treated with β1, β3, and β1+β3 antibodies, followed by MCMV infection. As described above, infectivity was determined by scoring e1-(early protein) positive cells. The percent infection as compared to infectivity seen with no treatment is shown on the y-axis of FIG. 4B. Strikingly, MCMV infectivity was reduced in GD25 cells to less than 10% as compared to the β1 integrin-expressing GD25β1 cells. Treating GD25 fibroblasts with β1 integrin-neutralizing antibodies had no additional inhibitory effect on MCMV infectivity. However, in cells expressing β1 integrins, such as GD25βI or NIH3T3, β1 integrin-neutralizing antibodies reduced MCMV infectivity to less then 20%. In contrast to HCMV infectivity, treating the cells with β3-neutralizing antibody had relatively little effect on MCMV infectivity. Because β3-integrin neutralizing antibodies do not significantly inhibit MCMV infection, but do inhibit HCMV infectivity, it can be concluded that MCMV utilizes a β1 integrin-specific entry pathway, while HCMV is capable of interacting with both β1 and β3 integrins.

β1 Integrins are Required for Cell-Cell Spread:

CMV dissemination in vivo is primarily mediated through cell-cell spread.[27] Most viruses utilize overlapping molecules and mechanisms for both entry and cell-cell viral transmission. To examine the role of β1 integrin in CMV spread of infection, GD25 or GD25β1 cells were infected with MCMV-GFP at a low MOI for a nine-day period. GD25 and GD25β1 cells were plated and infected with MCMV-GFP (100 pfu). Individual foci of infection were monitored over time for nine days and representative focus size for each day of infection by cell line was recorded photographically (data not shown). It is notable that both the number of entry events (see FIG. 4B) and the focus size were dramatically reduced in GD25 cells as compared to the cells expressing β1. These results strongly indicate that β1 integrins play a role in facilitating both viral entry and cell-cell dissemination of the virus.

HCMV Utilizes Integrins in a Past-Attachment Stage During the Entry Pathway:

During virus infection, integrins are utilized as primary viral attachment receptors or as post-attachment (fusion-activating) or internalization receptors.[11] To determine at which step in the HCMV entry pathway integrins are functioning, cell binding (i.e., attachment) experiments were performed, as well as assays to measure viral payload delivery into the cytoplasm (internalization). For the binding assays, virus was bound at 4° C. to allow for stable virus binding, but to restrict fusion and internalization. The results are depicted in FIG. 6A. FIG. 6A is a histogram showing the results of a series of assays wherein NHDF cells were treated with HCMV gB disintegrin-like peptides, null peptides, integrin-neutralizing antibodies, or soluble heparin at 4° C., followed by infection with HCMV. Attachment was measured by gB ELISA. Under conditions that maximally blocked HCMV infection (1 mM gB disintegrin-like peptide, 1:50 DE9, α2 and α6 integrin antibodies 20 µg/mL) there was no effect on HCMV attachment. As was previously known (and utilized here as a positive control), soluble heparin prevented virus attachment.[28] These data suggest that integrins are not involved in cellular attachment.

Next, an assay was performed that directly measured delivery of an internal virion component. The tegument phosphoprotein pp65 (UL83) (65 kDa), is delivered to the cytoplasm after virus-cell fusion and is targeted to the nucleus by a nuclear localization signal. FIG. 6B is a histogram showing the results of a series of assays wherein human fibroblasts were treated with various integrin-blocking agents, infected with HCMV, and then assayed for viral payload as measured by pp65 localization. Shown on the y-axis of FIG. 6B is the percent inhibition of pp65-positive cells as compared to untreated, but infected cells.

Uptake of pp65 is a direct measure of fusion and uncoating, but precedes any virus gene expression. Treatments that blocked HCMV infectivity (as measured by IE gene expression) also blocked uptake of this virion component. See FIG. 6B. Similarly, cells treated with the gB disintegrin-like peptide but not the gB disintegrin-like null peptide exhibited little uptake of the pp65 tegument protein (data not shown). These data support a role for α2β1, α2β1, and αVβ3 as HCMV entry receptors and further define the involvement of these specific integrins in mediating HCMV internalization, likely at the level of membrane fusion.

The gB Disintegrin-Like Peptide Exerts its Activity When Incorporated into a Larger Polypeptide Construct:

As noted above, a DNA sequence corresponding to amino acids 57-146 of HCMV AD 169 glycoprotein B disintegrin-like domain ("gB$_{DLD}$") was cloned, and the resulting polypeptide expressed in E. coli and purified. The gB$_{DLD}$ fragment in the context of the native amino terminus of HCMV gB is shown in FIG. 5. The underlined amino acids represent the gB disintegrin-like domain. The bold and underlined sequence represents the consensus integrin recognition motif and the sequence of the original disintegrin-like synthetic peptide.

A series of assays as described in the previous examples was performed on gB$_{DLD}$ to measure its ability to bind to NHDF cells, to measure the kinetics of that binding, and to determine if the binding was saturable. The results are shown in FIGS. 7, 8, and 9, respectively.

Figure 7:
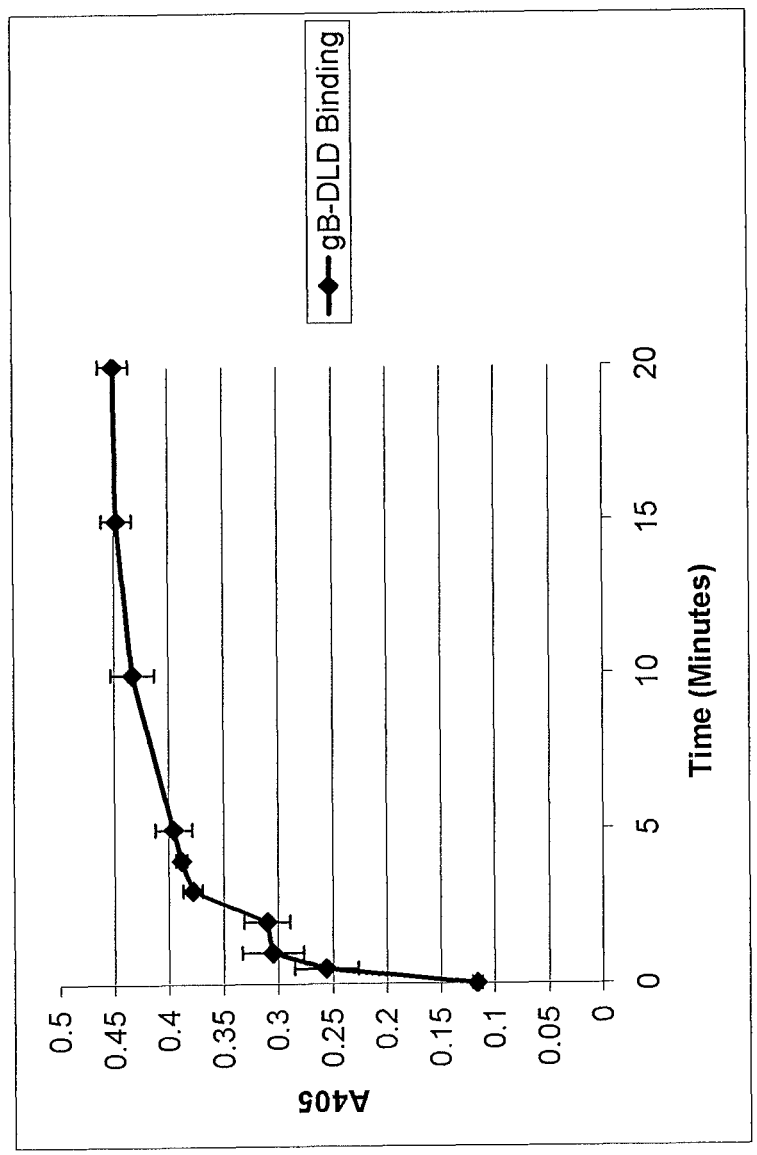
FIG. 7 is a graph depicting the kinetics of $gB_{DLD}$ binding to human fibroblasts.

FIG. 7 is a graph depicting the results of a gB$_{DLD}$ binding assay (performed as described previously). Here, binding was measured by absorbance at 405 nm. The graph shows that $gB_{DLD}$ binds human fibroblasts with rapid kinetics. To generate the data, human fibroblasts were incubated with $gB_{DLD}$ for the indicated times at 4° C. Cells were then washed, fixed and an ELISA was performed probing for the $gB_{DLD}$ C-terminal his-tag. Protein binding was found to be saturable and occur with rapid kinetics. HCMV attachment and entry kinetics are slower (~60-90 minutes) indicating that the $gB_{DLD}$-receptor interaction is not the initial attachment step, but occurs afterward initial attachment. After the rate-limiting attachment of virion to host cell, gB is able to engage its cell-surface receptor quickly and presumably then triggers virus-cell fusion.

Figure 8:
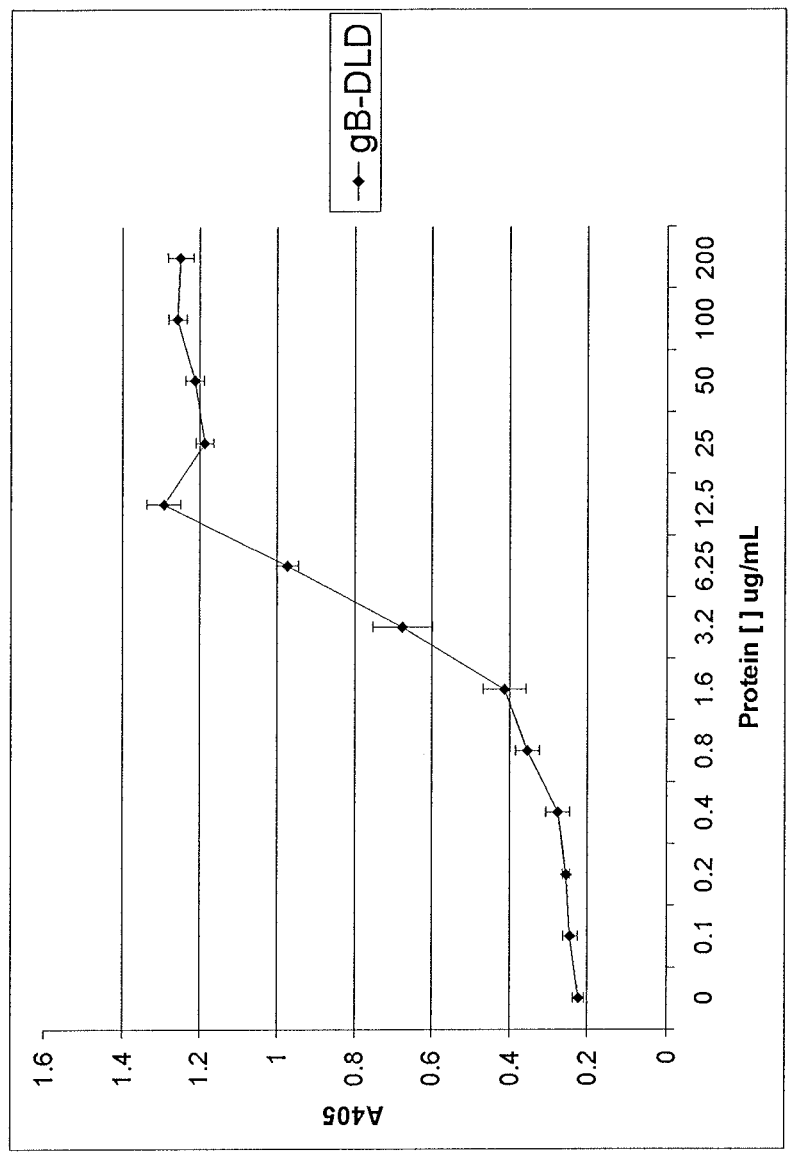
FIG. 8 is a graph demonstrating that the binding of $gB_{DLD}$ to human fibroblasts is dose-dependent and saturable.

FIG. 8 is a graph depicting $gB_{DLD}$ binding to human fibroblasts. As is readily apparent from FIG. 8, this binding is dose-dependent and saturable. Increasing amounts of $gB_{DLD}$ were added to cells for 60 minutes, after a BSA (1 mg/mL) blocking step. After three IVIES washes and two PBS washes, cells were fixed in 3% paraformaldehyde and a His-tag ELISA was performed to quantitate $gB_{DLD}$ bound to cells. Binding of $gB_{DLD}$ to fibroblast monolayers reached saturation at relatively low concentrations (12.5 μg/mL) indicating a specific interaction with the cellular receptor expressed at a moderate level.

Figure 9:
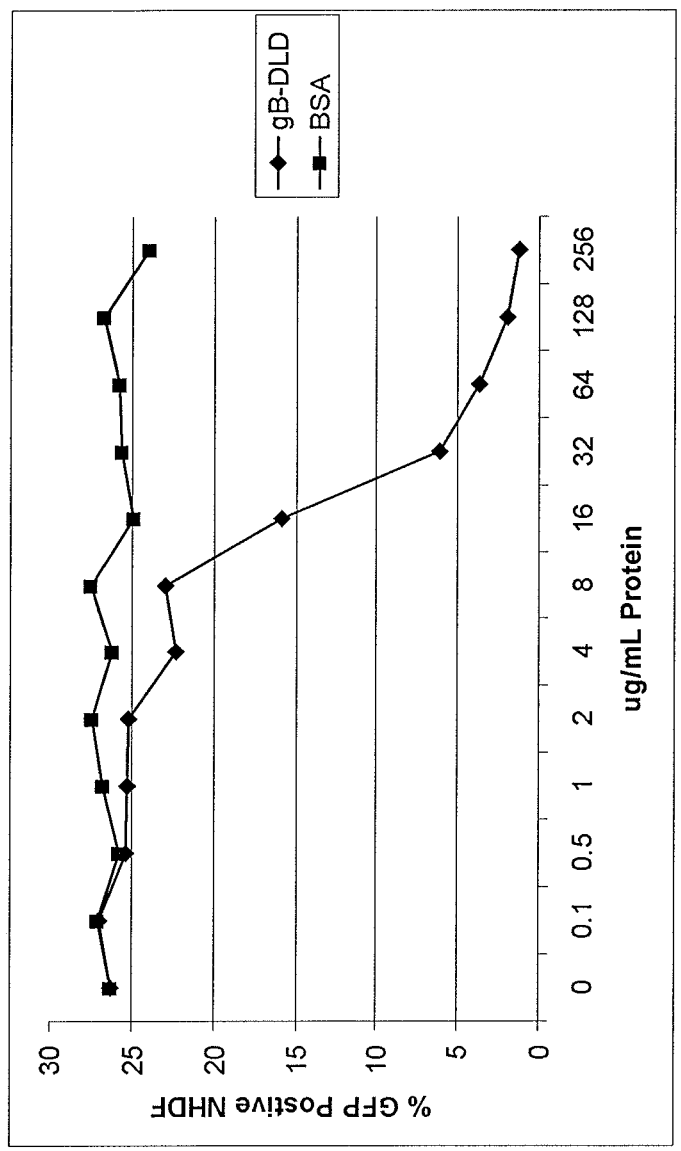
FIG. 9 is a graph demonstrating that $gB_{DLD}$ blocks HCMV infectivity of human fibroblasts.

FIG. 9 is a graph depicting the results of an assay to determine if $gB_{DLD}$ blocks NHDF cells from infection with HCMV. The infectivity assay was performed as described in the earlier examples. Briefly, $gB_{DLD}$ or BSA was added to human fibroblasts for 60 minutes. Cells were then washed, followed by HCMV-GFP challenge for 60 minutes. Cells were then citrate washed to remove any extracellular virus and incubated overnight. Flow cytometry was performed to assay for GFP positive versus total cells. As is readily observed from FIG. 9, $gB_{DLD}$ exerts a dose-dependent inhibition of HCMV infectivity in the cells tested. The $IC_{50}$ for HCMV neutralization by $gB_{DLD}$ was calculated to be 20.5 μg/mL or 1.96 μM. The striking efficiency of HCMV neutralization marks one of the most potent protein-based HCMV anti-viral agents characterized to date.

$gB_{DLD}$ Blocks HCMV Fusion:

To assess whether $gB_{DLD}$ was able to block HCMV infection at or before the virus-cell fusion event, virion envelope lipid was labeled with diI and dye transfer in cells pre-treated with $gB_{DLD}$ was measured directly. Cells were treated with $gB_{DLD}$ or BSA (320 μg/mL) or with soluble heparin (50 μg/mL) followed by diI-labeled HCMV or KSHV challenge. At 24 hours post-infection, cell monolayers were photographed to observed dye transfer (fusion) (data not shown). In cells treated with $gB_{DLD}$, complete block of HCMV fusion and gene expression was seen; however no block was observed with BSA. These results indicate that $gB_{DLD}$ binding to cells specifically blocks virus fusion and further that the block does not occur non-specifically, or through steric hindrance. As expected, soluble heparin blocks HCMV attachment to host cells (and therefore blocks any downstream events such as fusion or gene expression).

$gB_{DLD}$ Binds β1 Integrin:

To identify the cellular receptor for $gB_{DLD}$ we performed co-immunoprecipitation studies. Briefly, $gB_{DLD}$ was incubated with human fibroblast lysates and pulled down with nickel-conjugated agarose beads.

Figure 10:
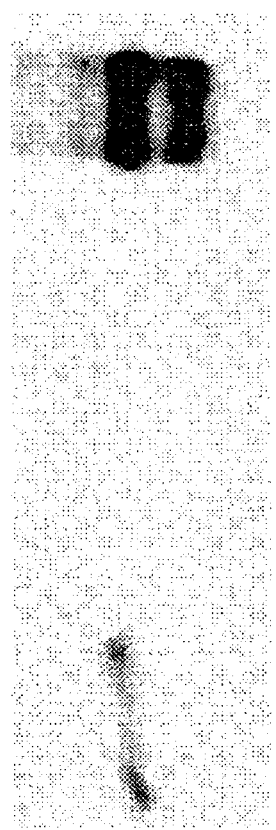
FIG. 10 is a Western blot showing that gB$_{DLD}$ interacts with β1 integrins.
Figure 11:
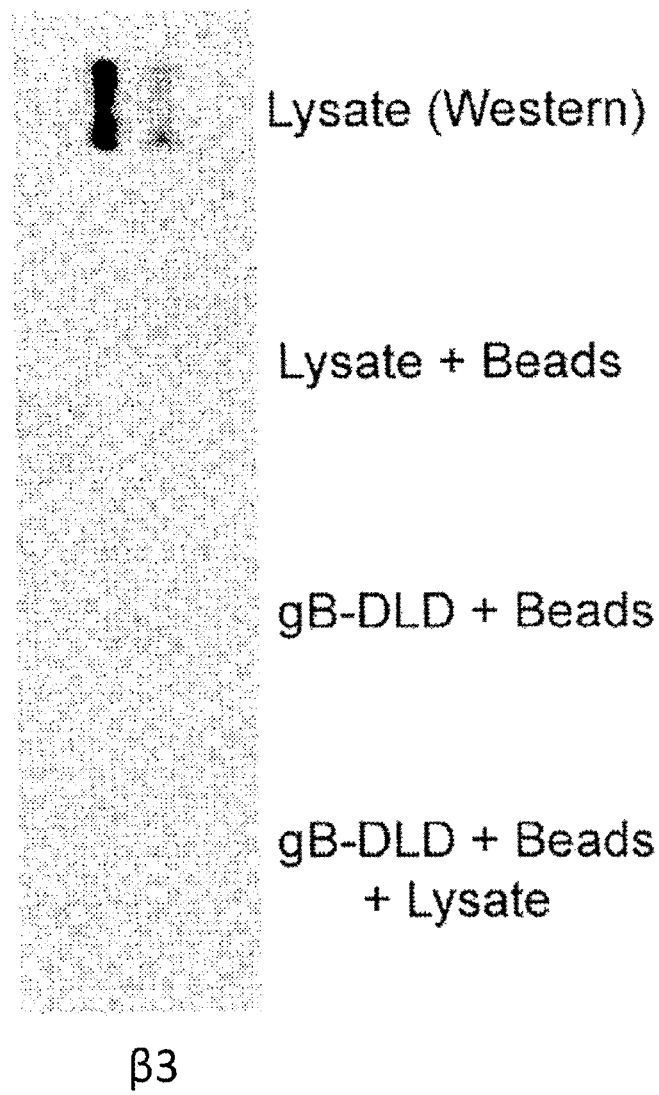
FIG. 11 is a Western blot showing that gB$_{DLD}$ does not interact with β3 integrins.

Because $gB_{DLD}$ contains a known β1 integrin binding motif, $gB_{DLD}$ bound to its cellular receptor was isolated by SDS-PAGE and then Western blotted for either β1 or β3 integrin. The resulting gels are shown in FIG. 10 (β1) and FIG. 11 (β3). As can readily be seen from the far right-hand lane in each of FIGS. 10 and 11, $gB_{DLD}$ interacts with β1 integrins, but does not interact with β3 integrins. In particular, FIG. 10 shows a robust pull down of β1 integrin when lysates were probed with $gB_{DLD}$ (FIG. 10, right-hand lane), but not with β3 under the same conditions (FIG. 11, right-hand lane). These data are the first demonstrated interaction between the gB disintegrin-like domain and its reported cellular receptor, β1 integrin.

$gB_{DLD}$ Triggers Cytoskeletal Rearrangements:

β1 integrins are known inducers of broad signal transduction events. Most notably, upon ligand binding, integrins are capable of dramatic reorganization of the cellular architecture. To test the role of $gB_{DLD}$ in mediating signaling events, we stimulated NHDF cells with buffer alone, $gB_{DLD}$, or a known cytoskeletal reorganizer (EGF), followed by actin staining with phalloidin. When compared to normal resting fibroblasts (buffer alone), both EGF and $gB_{DLD}$ triggered a dramatic reorganization of the cytoskeleton including the formation of filopodia (data not shown).

Significance of the Examples:

In accordance with the invention, each specific integrin heterodimer is capable of interacting with an overlapping set of ligands, a characteristic that many pathogens have evolved to exploit. Most viruses that utilize integrins as receptors are capable of engaging several different integrin heterodimers. Herein, a number of distinct methods all provide evidence for an integrin-dependent HCMV entry pathway, with specific involvement of α2β1, α6β1, and αVβ3 integrin heterodimers. In antibody blocking experiments, antibodies to α2, α6, αV, β1, and β3 inhibited HCMV entry and infectivity, but not host cell binding. In contrast, cells treated with α1, α3, α4, α5, and β1 (non-neutralizing) antibodies had no effect on virus entry or binding.

Inhibition of virus entry due to antibody blocking was not influenced by the relative abundance of each integrin heterodimer. HCMV entry was inhibited when antibodies blocked both highly expressed integrin heterodimers (αVβ3), as well as those with lower levels of expression (α6β1), but not the abundant α5 subunit, or the non-neutralizing β1, or scarce integrins such as α4. These observations eliminate the possibility that blocking of abundant integrins inhibited viral entry through steric hindrance or that blocking scarce heterodimers inhibited viral entry due to complete antibody saturation.

It is generally accepted that HCMV enters cells by direct fusion at the plasma membrane.[29] Thus, HCMV is the first enveloped virus to utilize integrins in a pH-independent attachment and fusion mechanism. However, several biologically crucial processes fitting the same criterion regularly occur within the human host. β1 integrins are utilized in myoblast-myoblast, osteoclast-osteoclast, macrophage-macrophage and vertebrate sperm-egg attachment and fusion events via unidentified mechanisms.[30-33] Although the inventors are not limited to any underlying mechanism, the present invention provides evidence that integrins function as HCMV receptors involved in virus entry, likely during the fusion step, as well as during cell-cell spread. This interaction seems to require the disintegrin-like domain found in the N-terminal region of gB. Interestingly, the vertebrate sperm glycoprotein ADAM 2 contains an N-terminal disintegrin-like domain that binds egg cell surface α6β1 integrin to mediate sperm-egg binding and fusion events. It remains a possibility that HCMV gB mimics ADAM 2 in its method of binding cellular integrins to promote the fusion event. The conservation of the disintegrin-like domain among herpesviruses suggests that elucidation of the precise mechanism of HCMV fusion may provide insight towards a conserved fusion mechanism within Herpesviridae, sperm-egg interactions and other integrin-mediated pH-independent fusion events.

Regardless of the underlying mechanism, the examples clearly indicate that gB disintegrin-like peptides are useful to inhibit infection of cells by various cytomegaloviruses, and related viruses.

It has been shown that the immune sensor Toll-like Receptor 2 (TLR 2) is activated in response to HCMV infection, thereby resulting in induction of innate immune responses.[34] In addition, a recent report indicates that EGFR functions as a HCMV receptor in certain cell types.[7] In combination with the literature and the examples presented herein, a CMV entry pathway can be modeled in which a multi-component complex forms, allowing the engagement of multiple receptors and the formation of a functional signaling platform. The proposed model places cellular integrins in a central ligating role. A connection between β1 and β2 integrins and an enhancement of TLR signaling has been described.[35,36] Further, both β1 and β3 integrins have been shown to associate with EGFR, activate EGFR in a ligand-independent manner (i.e., activate EGFR through integrin binding)[37,38] and synergistically enhance EGFR signaling.[39] At present, the sequence of HCMV engagement with TLR 2, EGFR, and integrin receptors remains undefined. Also under investigation are the coordination and signaling properties of each of these receptors in both entry and immune detection.

Synthetic peptides of the novel gB disintegrin-like domain inhibit both HCMV and MCMV infectivity, thus implicating this sequence in the CMV-integrin interaction. It has also been found that the disintegrin-like domain consensus sequence is completely conserved among beta herpesviruses, including human herpesvirus-6, human herpesvirus-7 and other animal Herpesviruses. The gamma herpesviruses Epstein Barr Virus (EBV) and Kaposi's sarcoma-associated herpesvirus (KSHV) both have been shown to utilize integrins as entry receptors via an RGD sequence.[40,41] Upon further examination, however, both viruses also contain the conserved gB disintegrin-like domain. While it is thought that KSHV primarily utilizes α3β1 in its entry, antibody blocking experiments also implicate α2β1.[41] Both proposed heterodimers typically engage integrins in an RGD-independent manner,[42] provoking questions of the importance of the disintegrin-like domain in the entry of these viruses as well. The sequence analyses performed in the course of this work revealed that while alpha herpesviruses lack the gB disintegrin-like domain, herpes simplex-1 (HSV-1) contains an RGD sequence in gH, a gene essential for virus fusion (data not shown). The presence of a conserved disintegrin-like domain and/or an RGD sequence among most herpesviruses implicates cellular integrins as coreceptors throughout the medically important Herpesviridae.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Ljungman, P. Cytomegalovirus infections in transplant patients. *Scand J Infect Dis Suppl* 100, 59-63 (1996).
2. Ramsay, M. E., Miller, E. & Peckham, C. S. Outcome of confirmed symptomatic congenital cytomegalovirus infection. *Arch Dis Child* 66, 1068-9 (1991).
3. Sinzger, C. et al. Tropism of human cytomegalovirus for endothelial cells is determined by a post-entry step dependent on efficient translocation to the nucleus. *J Gen Virol* 81, 3021-35 (2000).
4. Ibanez, C. E., Schrier, R., Ghazal, P., Wiley, C. & Nelson, J. A. Human cytomegalovirus productively infects primary differentiated macrophages. *J Virol* 65, 6581-8 (1991).
5. Myerson, D., Hackman, R. C., Nelson, J. A., Ward, D. C. & McDougall, J. K. Widespread presence of histologically occult cytomegalovirus. *Hum Pathol* 15, 430-9 (1984).
6. Nowlin, D. M., Cooper, N. R. & Compton, T. Expression of a human cytomegalovirus receptor correlates with infectibility of cells. *J Virol* 65, 3114-21 (1991).
7. Wang, X., Huong, S. M., Chiu, M. L., Raab-Traub, N. & Huang, E. S. Epidermal growth factor receptor is a cellular receptor for human cytomegalovirus. *Nature* 424, 456-61 (2003).
8. Valyi-Nagy, T., Bandi, Z., Boldogh, I. & Albrecht, T. Hydrolysis of inositol lipids: an early signal of human cytomegalovirus infection. *Arch Virol* 101, 199 207 (1988).
9. Kowalik, T. F. et al. Multiple mechanisms are implicated in the regulation of NFkappa B activity during human cytomegalovirus infection. *Proc Natl Acad Sci USA* 90, 1107-11 (1993).
10. Diosi, P., Babusceac, L. & David, C. Cytomegalovirus type cytopathic changes in spontaneously degenerating human embryonic cell cultures. *Nature* 214, 419-20 (1967).
11. Triantafilou, K., Takada, Y. & Triantafilou, M. Mechanisms of integrin-mediated virus attachment and internalization process. *Crit Rev Immunol* 21, 311-22 (2001).
12. Cary, L. A., Han, D.C. & Guan, J. L. Integrin-mediated signal transduction pathways. *Histol Histopathol* 14, 1001-9 (1999).
13. Berman, A. E. & Kozlova, N. I. Integrins: structure and functions. *Membr Cell Biol* 13, 207-44 (2000).
14. Stone, A. L., Kroeger, M. & Sang, Q. X. Structure-function analysis of the ADAM family of disintegrin-like and metalloproteinase-containing proteins (review). *J Protein Chem* 18, 447-65 (1999).
15. Eto, K. et al. Functional classification of ADAMS based on a conserved motif for binding to integrin alpha 9beta 1: implications for sperm-egg binding and other cell interactions. *J Biol Chem* 277, 17804-10 (2002).
16. Spear, P. G. & Longnecker, R. Herpesvirus entry: an update. *J Virol* 77, 10179-85 (2003).
17. Boyle, K. A., Pietropaolo, R. L. & Compton, T. Engagement of the cellular receptor for glycoprotein B of human cytomegalovirus activates the interferon responsive pathway. *Mol Cell Biol* 19, 3607-13 (1999).
18. Boyle, K. A. & Compton, T. Receptor-binding properties of a soluble form of human cytomegalovirus glycoprotein B. *J Virol* 72, 1826-33 (1998).
19. Lantto, J., Fletcher, J. M. & Ohlin, M. Binding characteristics determine the neutralizing potential of antibody fragments specific for antigenic domain 2 on glycoprotein B of human cytomegalovirus. *Virology* 305, 201-9 (2003).
20. Gicklhorn, D., Eickmann, M., Meyer, G., Ohlin, M. & Radsak, K. Differential effects of glycoprotein B epitope-specific antibodies on human cytomegalovirus induced cell-cell fusion. *J Gen Virol* 84, 1859-62 (2003).
21. Chang, H. H. et al. Facilitation of cell adhesion by immobilized dengue viral nonstructural protein 1 (NS1): arginine-glycine-aspartic acid structural mimicry within the dengue viral NS1 antigen. *J Infect Dis* 186, 743-51 (2002).

22. Bergelson, J. M., Shepley, M. P., Chan, B. M., Hemler, M. E. & Finberg, R. W. Identification of the integrin VLA-2 as a receptor for echovirus 1. *Science* 255, 1718-20 (1992).
23. Bergelson, J. M. et al. Infection by echoviruses 1 and 8 depends on the alpha 2 subunit of human VLA-2. *J Virol* 67, 6847-52 (1993).
24. Ciarlet, M. et al. VLA-2 (alpha2beta1) integrin promotes rotavirus entry into cells but is not necessary for rotavirus attachment. *J Virol* 76, 1109-23 (2002).
25. Graham, K. L. et al. Integrin-using rotaviruses bind alpha2beta1 integrin alpha2 I domain via VP4 DGE sequence and recognize alphaXbeta2 and alphaVbeta3 by using VP7 during cell entry. *J Virol* 77, 9969-78 (2003).
26. Sakai, T., Peyruchaud, O., Fassler, R. & Mosher, D. F. Restoration of beta1A integrins is required for lysophosphatidic acid-induced migration of beta1-null mouse fibroblastic cells. *J Biol Chem* 273, 19378-82 (1998).
27. Gerna, G. et al. Human cytomegalovirus replicates abortively in polymorphonuclear leukocytes after transfer from infected endothelial cells via transient microfusion events. *J Virol* 74, 5629-38 (2000).
28. Compton, T., Nowlin, D. M. & Cooper, N. R. Initiation of human cytomegalovirus infection requires initial interaction with cell surface heparan sulfate. *Virology* 193, 834-41 (1993).
29. Compton, T., Nepomuceno, R. R. & Nowlin, D. M. Human cytomegalovirus penetrates host cells by pH-independent fusion at the cell surface. *Virology* 191, 387-95 (1992).
30. Almeida, E. A. et al. Mouse egg integrin alpha 6 beta 1 functions as a sperm receptor. *Cell* 81, 1095-104 (1995).
31. Boissy, P., Machuca, I., Pfaff, M., Ficheux, D. & Jurdic, P. Aggregation of mononucleated precursors triggers cell surface expression of alphavbeta3 integrin, essential to formation of osteoclast-like multinucleated cells. *J Cell Sci* 111 (Pt 17),2563-74 (1998).
32. McNally, A. K. & Anderson, J. M. Beta1 and beta2 integrins mediate adhesion during macrophage fusion and multinucleated foreign body giant cell formation. *Am J Pathol* 160, 621-30 (2002).
33. Schwander, M. et al. Beta1 integrins regulate myoblast fusion and sarcomere assembly. *Dev Cell* 4, 673-85 (2003).
34. Compton, T. et al. Human cytomegalovirus activates inflammatory cytokine responses via CD14 and Toll-like receptor 2. *J Virol* 77, 4588-96 (2003).
35. Ogawa, T., Asai, Y., Hashimoto, M. & Uchida, H. Bacterial fimbriae activate human peripheral blood monocytes utilizing TLR2, CD14 and CD11a/CD18 as cellular receptors. *Eur J Immunol* 32, 2543-50 (2002).
36. Perera, P.Y. et al. CD11b/CD18 acts in concert with CD14 and Toll-like receptor (TLR) 4 to elicit full lipopolysaccharide and taxol-inducible gene expression. *J Immunol* 166, 574-81 (2001).
37. Moro, L. et al. Integrins induce activation of EGF receptor: role in MAP kinase induction and adhesion-dependent cell survival. *Embo J* 17, 6622-32 (1998).
38. Jones, P. L., Crack, J. & Rabinovitch, M. Regulation of tenascin-C, a vascular smooth muscle cell survival factor that interacts with the alpha v beta 3 integrin to promote epidermal growth factor receptor phosphorylation and growth. *J Cell Biol* 139, 279-93 (1997).
39. Miyamoto, S., Teramoto, H., Gutkind, J. S. & Yamada, K. M. Integrins can collaborate with growth factors for phosphorylation of receptor tyrosine kinases and MAP kinase activation: roles of integrin aggregation and occupancy of receptors. *J Cell Biol* 135, 1633-42 (1996).
40. Tugizov, S. M., Berline, J. W. & Palefsky, J. M. Epstein-Barr virus infection of polarized tongue and nasopharyngeal epithelial cells. *Nat Med* 9, 307-14 (2003).
41. Akula, S. M., Pramod, N. P., Wang, F. Z. & Chandran, B. Integrin alpha3beta1 (CD 49c/29) is a cellular receptor for Kaposi's sarcoma-associated herpesvirus (KSHV/HHV-8) entry into the target cells. *Cell* 108, 407-19 (2002).
42. Ruoslahti, E. RGD and other recognition sequences for integrins. *Annu Rev Cell Dev Biol* 12, 697-715 (1996).
43. Henry, S. C. et al. Enhanced green fluorescent protein as a marker for localizing murine cytomegalovirus in acute and latent infection. *J Virol Methods* 89, 61-73 (2000).
44. Schoppel, K. et al. Antibodies specific for the antigenic domain 1 of glycoprotein B (gpUL55) of human cytomegalovirus bind to different substructures. *Virology* 216, 133-45 (1996).
45. Ciocco-Schmitt, G. M. et al. Identification and characterization of novel murine cytomegalovirus M112-113 (e1) gene products. *Virology* 294, 199-208 (2002).
46. Sanchez, V. et al. (2002) Viable human cytomegalovirus recombinant virus with an internal deletion of the IE2 86 gene affects late stages of viral replication. *J Virol* 76 (6), 2973-2989.
47. Superti, F. et al. (1987) Entry pathway of vesicular stomatitis virus into different host cells. *J Gen Virol* 68 (Pt 2), 387-399.
48. Feire, A. L. et al. (2004) Cellular integrins function as entry receptors for human cytomegalovirus via a highly conserved disintegrin-like domain. *Proc Natl Acad Sci USA* 101 (43), 15470-15475.

What is claimed is:

1. A method of inhibiting viral infection of an animal host cell, the method comprising administering to the host cell an antiviral-effective amount of an active agent comprising a purified antibody that binds selectively to an integrin-binding, gB disintegrin-like peptide comprising the consensus sequence RX5-8DLXXFX5C (SEQ. ID. NOS: 1-4), and wherein the purified antibody binds to the consensus sequence.

2. The method of claim 1, wherein the purified antibody binds selectively to an integrin-binding, gB disintegrin-like peptide comprising the amino acid sequence RVCSMAQGTDLI RFERNIVC (SEQ. ID. NO: 5).

3. The method of claim 1, wherein the purified antibody binds selectively to an integrin-binding, gB disintegrin-like peptide comprising residues 91-111 of glycoprotein B of human cytomegalovirus.

4. The method of claim 1, wherein the purified antibody inhibits engagement of virions with cellular integrins.

5. The method of claim 1, wherein the purified antibody inhibits internalization of virus of family Herpesviridae (V.C. 31) into the host cell.

6. The method of claim 1, wherein the purified antibody inhibits internalization of virus of family Herpesviridae, subfamily Beta herpesviridae (V.C. 31.2) into the host cell.

7. The method of claim 1, wherein the purified antibody inhibits internalization of virus of family Herpesviridae, subfamily Beta herpesviridae, genus Cytomegalovirus (V.C. 31.2.1) into the host cell.

8. The method of claim 1, wherein a purified monoclonal antibody is administered to the host cell.

9. The method of claim 1, wherein a purified polyclonal antibody is administered to the host cell.

10. A composition comprising an antiviral-effective amount of a purified antibody that binds specifically to an integrin-binding, gB disintegrin-like peptide comprising the consensus sequence RX5-8 DLXXFX5 C (SEQ. ID. NOS: 1-4), and wherein the purified antibody binds to the consensus sequence.

11. The composition of claim 10, further comprising, in combination, a pharmaceutical carrier suitable for administration by a route selected from the group consisting of parenterally, orally, subcutaneously, and topically.

12. The composition of claim 10, wherein the purified antibody binds selectively to an integrin-binding, gB disintegrin-like peptide comprising the amino acid sequence RVCSMAQGTDLIRFERNIVC (SEQ. ID. NO: 5), and wherein the purified antibody binds to the amino acid sequence.

13. The composition of claim 10, wherein the purified antibody binds selectively to an integrin-binding, gB disintegrin-like peptide comprising residues 91-111 of glycoprotein B of human cytomegalovirus, and wherein the purified antibody binds to residues 91-111 of glycoprotein B of human cytomegalovirus.

14. The composition of claim 10, wherein the purified antibody inhibits engagement of virions with cellular integrins.

15. The composition of claim 10, wherein the purified antibody is a monoclonal antibody.

16. The composition of claim 10, wherein the purified antibody is a polyclonal antibody.

17. A purified antibody that binds specifically to an integrin-binding, gB disintegrin-like peptide comprising the consensus sequence $RX_{5-8}DLXXFX_5C$ (SEQ. ID. NOS: 1-4)), and wherein the purified antibody binds to the consensus sequence.

18. The purified antibody of claim 17, wherein the antibody binds selectively to an integrin-binding, gB disintegrin-like peptide comprising the amino acid sequence RVCSMAQGTDLIRFERNIVC (SEQ. ID. NO: 5), and wherein the purified antibody binds to the amino acid sequence.

19. The purified antibody of claim 17, wherein the antibody binds selectively to an integrin-binding, gB disintegrin-like peptide comprising residues 91-111 of glycoprotein B of human cytomegalovirus, and wherein the purified antibody binds to residues 91-111 of glycoprotein B of human cytomegalovirus.

20. The purified antibody of claim 17, wherein the antibody inhibits engagement of virions with cellular integrins.

21. The purified antibody of claim 17, wherein the antibody inhibits internalization of virus of family Herpesviridae (V.C. 31) into host cells.

22. The purified antibody of claim 17, wherein the antibody inhibits internalization of virus of family Herpesviridae, subfamily Beta herpesvirinae (V.C. 31.2) into host cells.

23. The purified antibody of claim 17, wherein the antibody inhibits internalization of virus of family Herpesviridae, subfamily Beta herpesvirinae, genus Cytomegalovirus (V.C. 31.2.1) into host cells.

24. The purified antibody of claim 17, wherein the antibody is a monoclonal antibody.

25. The purified antibody of claim 17, wherein the antibody is a polyclonal antibody.

* * * * *